US008916609B2

(12) United States Patent
Ward et al.

(10) Patent No.: US 8,916,609 B2
(45) Date of Patent: Dec. 23, 2014

(54) COMPOUNDS AS L-CYSTINE CRYSTALLIZATION INHIBITORS AND USES THEREOF

(75) Inventors: Michael D. Ward, New York, NY (US); Zina Zhu, Elmhurst, NY (US)

(73) Assignee: New York University, New York, NY (US)

( * ) Notice: Subject to any disclaimer, the term of this patent is extended or adjusted under 35 U.S.C. 154(b) by 18 days.

(21) Appl. No.: 13/491,816

(22) Filed: Jun. 8, 2012

(65) Prior Publication Data

US 2012/0316236 A1 Dec. 13, 2012

Related U.S. Application Data

(60) Provisional application No. 61/495,585, filed on Jun. 10, 2011.

(51) Int. Cl.
*A61K 31/132* (2006.01)
*A61K 31/095* (2006.01)
*A61K 31/225* (2006.01)
*A61K 31/195* (2006.01)

(52) U.S. Cl.
CPC ............ *A61K 31/132* (2013.01); *A61K 31/095* (2013.01); *A61K 31/195* (2013.01); *A61K 31/225* (2013.01)
USPC .......................................................... 514/548

(58) Field of Classification Search
USPC ........................................................ 514/548
See application file for complete search history.

(56) References Cited

U.S. PATENT DOCUMENTS 5,019,596 A * 5/1991 Reiner et al. .................. 514/578

OTHER PUBLICATIONS

Salmon, Intracellular Cystine Loading Inhibits Transport in the Rabbit Proximal Convoluted Tubule, J. Clin. Invest., 85(2): 340-344, 1990.*
Dolin, D.J., et al., "Effect of Cystine-Binding Thiol Drugs on Unrinary Dystine Capacity in Patients with Cystinuria," Journ of Endourology, vol. 19, No. 3, Apr. 2005, pp. 429-432.
Mattoo, A., et al., "Cystinuria," Seminars in Nephrology. vol. 28, No. 2, Mar. 2008, pp. 181-191.
Moe, Orson W., "Kidney stones: pathophysiology and medical management," Lancet 2006, vol. 367, pp. 333-344.
Becker, Gavin, "Cystine stones," Nephrology 2007; vol. 12, pp. S4-S10.
Nakagawa, Y., et al., "Clinical Use of Cystine Supersaturation Measurements," The Journal of Urology, vol. 164, Nov. 2000, pp. 1481-1485.
Moggach, S.A., et al., "The effect of pressure on the crystal structure of hexagonal l-cystine," Journal of Synchrotron Radiation (2005), 12, pp. 598-607, ISSN 0909-0495.

Dahaou, S., et al., "CCD Charge Density Study on Crystals with Large Unit Cell Parameters: The case of Hexagonal L-Cystine," J. Phys. Chem. A, 1999, vol. 103, pp. 6240-6250.
Girija, E.K., et al., "Crystallization of cystine," Journal of Materials Science: Materials in Medicine, vol. 6 (1995), pp. 617-619.
Fujiki, Y., et al., "Anisotropic Decoration of Gold Nanoparticles onto Specific Crystal Faces of Organic Single Crystals**," Angewandte Chemie Int. Ed., 2006, vol. 45, pp. 4764-4767.
Chaney, M.O., et al., "The Crystal and Molecular Structure of Tetragonal L-Cystine," Acta Cryst B, Mar. 15, 1974; B30: 711-716.
Steinrauf, L.K., et al., "The Cyrstal Structue of L-Cystine Hdrochloride," J. Amer. Chem. So., 1958; 80(15): 3835-3838.
Kominani, S., "X-Ray Diffractionand Electron Spin Resonance Studies of Single Crystals of Copper (II) Doped L-Systine Dihydrochloride Dihydrate," J. Phys. Chem., 1976, Vo. 80, No. 2, pp. 203-210.
Carta, R., et al., "Solubilities of L-Cystine, L-Tyrosine, L-Leucine, and Glycine in Aqueous Solutions at Various pHs and NaCl Concentrations," J. Chem. Eng. Data, 1996: vol. 41, No. 3, pp. 414-417.
Kuzmenko, I., et al., "Formation of Chiral Interdigitated Multilayers at the Air-Liquid Interface Through Acid-Base Interactions," Science, vol. 274, Dec. 20, 1996, pp. 2046-2049.
Weinbach, S.P., et al., "Control of Structure and Growth of Polymorphic Crystalline Thin Films of Amphiphilic Molecules on Liquid Surfaces," Science, vol. 264, Jun. 10, 1994, pp. 1566-1570.
Graether, S.P., et al., "B-Helix Structure and ice-binding properties of a hyperactive antifreeze protein from an insect," Nature, vol. 406, Jul. 20, 2000, pp. 325-328.
Graham, L.A., et al., "Glycine-Rich Antifreeze Proteins from Snow Fleas," Science, vol. 310, Oct. 21, 2005, at p. 461.
Liou, Y., et al., "Mimicry of ice structure by surface hydroxyls and water of a B-helix antifreeze protein," Nature, vol. 406, Jul. 20, 2000, pp. 322-324.
Sonnichsen, F.D., et al., "The Nonhelical Structure of Antifreeze Protein Type III," Science, vol. 259, Feb. 19, 1993, pp. 1154-1157.
Weissbuch, I., et al., "Molecular Recognition at Crystal Interfaces," Articles, Aug. 9, 1991, pp. 637-645.
Orme, C.A., et al., "Formation of chiral morphologies through selective binding of amino acids to calcite surface steps," Nature, vol. 411, Jun. 14, 2001, pp. 775-779.
Stephenson, A.E., et al., "Peptides Enhance Magnesium Signature in Calcite: Insights into Origins of Vital Effects," Science, vol. 322, Oct. 31, 2008, pp. 724-727.
Sheng, X., et al., "Adhesion at calcium oxalate crystal surfaces and the effect of urinary constituents," PNAS, Jan. 11, 2005, vol. 102, No. 2, pp. 267-272.
De Yoreo, J.J., et al., "Shaping Crystals and Biomolecules," Science 306, 1301 (2004; DOI: 10.1126/science.1100889.

(Continued)

*Primary Examiner* — Jeffrey S. Lundgren
*Assistant Examiner* — Zenab Olabowale
(74) *Attorney, Agent, or Firm* — Klauber & Jackson LLC

(57) ABSTRACT

A method of preventing or inhibiting L-cystine crystallization is disclosed, using the compounds of formula I:

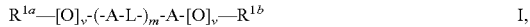

wherein A, L, $R^{1a}$, $R^{1b}$, m, and v are as described herein. The compounds may be prepared as pharmaceutical compositions, and may be used for the prevention and treatment of conditions that are causally related to L-cystine crystallization, such as comprising (but not limited to) kidney stones.

18 Claims, 4 Drawing Sheets

(56) References Cited

OTHER PUBLICATIONS

Grohe, B., et al., "Control of Calcium Oxalate Crystal Growth by Face-Specific Adsorption of an Osteopontin Phosphopeptide," J. Am. Chem. Soc. 2007, vol. 129, pp. 14946-14951.

Sizemore, J.P., et al., "A New Model for the Effect of Molecular Imposters on the Shape of Faceted Molecular Crystals," Crystal Growth & Design, 2009, vol. 9, No. 6, pp. 2637-2645.

Jung, T., et al., "Probing Crystallization of Calcium Oxalate Monohydrate and the Role of Macromolecule Additives with in Situ Atomic Force Microscopy," Langmuir, 2004, vol. 20, pp. 8587-8596.

Kessler, A., et al., "Antioxidant Effect of Cysteamine in Brain Cortex of Young Rats," Neurochem. Res. (2008) vol. 33, pp. 737-744.

Wilmer, M.J., et al., "Cystine Dimethylester Model of Cystinosis: Still Reliable?" Pediatric Research, vol. 62, No. 2, 2007, pp. 151-155.

Foreman, J.W., et al., "Effect of Cystine Dimethylester on Renal Solute Handling and Isolated Renal Tubule Transport in the Rat: A New Model of the Fanconi Syndrome," Metabolism, vol. 36, vol. 12, Dec. 1987, pp. 1185-1191.

Kallistratos, V.G., et al., "Experimentelle Untersuchungen zur Frage der chemischen Auflosung von Cystinsteinen," Arzneimittel-Forschung, 1972: vol. 22, No. 9, pp. 1434.

Konigsberger, E., et al., "Solubility of L-Cystine in NaCl and Artificial Urine Solutions," Monatschefte Fur Chemie, 2000; vol. 131, vol. 1, pp. 39-45.

Oughton, B.M., et al., "The Crystal Structure of Hexagonal L-Cystine," Acta Crystallographica, 1959, vol. 12, No. 5, pp. 396-404.

Vijayalakshmi, B.K., et al., "Crystal and Molecular Structue of L-Cystine Dimethyl Ester Dihydrochloride Monohydrate," Acta Cryst B, 1975; B31 (Apr. 15), pp. 993-998.

Eldjarn, L., et al., "The Rationale of Mixed Disulphides in the Treatment of Cystinuria," Scandinav. J. Clin. & Lab Investigation, vol. 16, 1964, pp. 153-164.

Theriault, Y., et al., "A nuclear magnetic resonance study of the equilibria and kinetics of the reaction of penicillamine with cystine and related disulfides," Canadian J. Chem, 1985; vol. 63, No. 8, pp. 2225-2231.

\* cited by examiner

Inhibitory effect of different esters of L-cystine (0.015mM)

COMPOUNDS AS L-CYSTINE CRYSTALLIZATION INHIBITORS AND USES THEREOF

RELATED APPLICATION

The present application claims the benefit under 35 U.S.C. §119 of U.S. Provisional Application Ser. No. 61/495,585, filed Jun. 10, 2011. The content of said provisional application is hereby incorporated by reference in its entirety.

FIELD OF THE INVENTION

The present invention relates to the identification of compounds that inhibit L-cystine crystallization, and the use of such compounds and compositions thereof to prevent or slow L-cystine crystal production. This invention also relates to methods for preventing and/or treating conditions that are causally related to L-cystine crystallization, such as comprising (but not limited to) kidney stones, using the compounds of the invention. It is to be understood that such compounds may be used either alone or in combination with other compounds having the activity set forth herein.

BACKGROUND OF THE INVENTION

L-cystine stones account for less than 2% of adult kidney stones and affect more than 100,000 U.S. patients. L-cystine stones, which are larger and are more likely to cause chronic kidney disease than calcium oxalate monohydrate (COM) stones, form as a consequence of excessive levels of L-cystine in the urine due to defective reabsorption of filtered cystine [1]. This autosomal recessive disorder is caused by mutations in one of two genes coding for components of proximal renal tubule amino acid transporters. Affected genes are either SLC3A1 on chromosome 2 leading to type A cystinuria, or SLC7A9 on chromosome 19 leading to type B [2]. The low solubility of L-cystine [3] induces rapid crystallization, which is followed by aggregation to generate stones (FIG. 1A) with sizes that can achieve centimeter dimensions.

Current treatments include high fluid intake [4], increasing urine pH through ingestion of alkalinizing potassium or sodium salts [4, 5], or the administration of L-cystine binding thiol drugs (CBTDs), such as D-penicillamine (HS—C(CH$_3$)$_2$—CH(NH$_2$)—COOH) and α-mercaptopropionylglycine (α-MPG or tiopronin: HS—CHCH$_3$—CO—NH—CH$_2$—COOH), which undergo a thiol-disulfide exchange with L-cystine to generate more soluble products [1]. These treatments suppress, but often do not completely prevent, stone formation. Thiol drugs have an unpleasant odor and can cause adverse side-effects, such as nausea, fever, fatigue, and skin allergies [5]. CBTDs are accompanied by high fluid intake to achieve a cystine excretion rate of 2.9 mM/day (i.e. urine volumes of 3 L/day) [4] and thiol excretion rates of 0.5-6 mM/day. A shortcoming of thiol drugs, however, is their inadequacy to reduce and solubilize large enough quantities of L-cystine in the urine based on acceptable dosages (up to 2000 mg/day), which are limited due to hypersensitivity and toxicity concerns.

Therefore, there is a need for an improved method to prevent, inhibit or slow L-cystine crystal production, and it is toward the fulfillment of that need that the present invention is directed.

SUMMARY OF THE INVENTION

In a first aspect, the present invention relates to the prevention of L-cystine kidney stones based on crystal growth inhibition via the binding of tailored growth inhibitors to specific crystal surfaces through molecular recognition.

Thus, one aspect of the invention provides a method for preventing, inhibiting or slowing the growth of L-cystine crystallization comprising administering an effective amount of a compound of formula I:

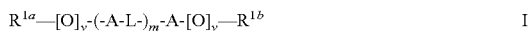

or a pharmaceutically acceptable salt, solvate, cocrystal, or prodrug thereof, and stereoisomers, tautomers and isotopic variants thereof; and wherein
each A is independently

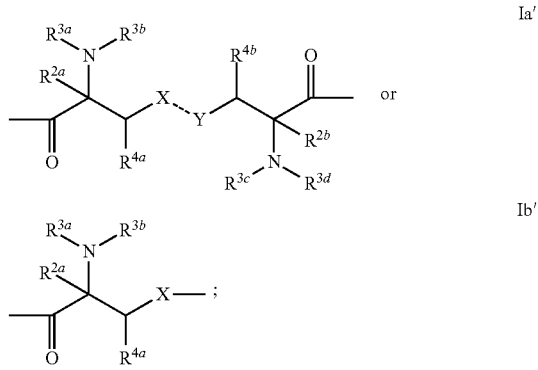

each X and Y is independently S, S(O), S(O)$_2$, or C(R$^5$)$_q$; each R$^{2a}$, R$^{2b}$, R$^{3a}$, R$^{3b}$, R$^{3c}$, R$^{3d}$, R$^{4a}$, and R$^5$ is independently selected from H, substituted or unsubstituted alkyl, substituted or unsubstituted aryl, substituted or unsubstituted aralkyl, and substituted or unsubstituted cycloalkyl; the subscript q is 1 or 2;
the dotted bond is a single or a double bond;
provided that when one of X and Y is S, S(O), or S(O)$_2$, then the dotted bond is a single bond;
L is —O—C$_1$-C$_6$ alkylene-O—, —O-aryl-O—, or a group —O—(CH$_2$—CH$_2$—O—)$_t$—; the subscript t is 1-10; the subscript m is 0-10; and
each R$^{1a}$ and R$^{1b}$ is independently selected from substituted or unsubstituted alkyl, substituted or unsubstituted aryl, substituted or unsubstituted aralkyl, and substituted or unsubstituted cycloalkyl; and each subscript v is 0 or 1;
In one particular embodiment, with respect to formula I, when A is Ia', both X and Y are S, S(O), or S(O)$_2$, and m is 0, then each subscript v is 0.
In one embodiment, with respect to formula I, A is

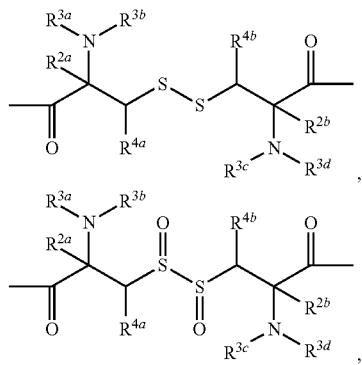

-continued

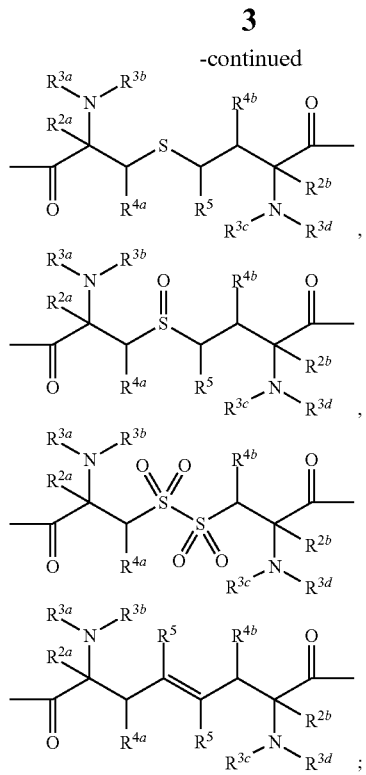

and wherein $R^{2a}$, $R^{2b}$, $R^{3a}$, $R^{3b}$, $R^{3c}$, $R^{3d}$, $R^{4a}$, $R^{4b}$, and $R^5$ are as described for formula I.

In one embodiment, with respect to formula I, subscript m is 1-5.

In one embodiment, with respect to formula I, L is —O—CH$_2$—O—. In another embodiment L is —O—CH$_2$—CH$_2$—O—.

In one embodiment, with respect to formula I, L is

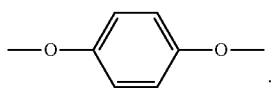

In one embodiment, with respect to formula I, L is —O—(CH$_2$—CH$_2$—O)$_t$—; and the subscript t is 1; In another embodiment the subscript t is 2.

In one embodiment, with respect to formula I, subscript m is 0.

In one embodiment, with respect to formula I, the subscript m is 0; and the subscript v is 0.

In one embodiment, with respect to formula I, subscript m is 0; and the compound is according to formula II:

   II;

and wherein A, $R^{1a}$ and $R^{1b}$ are as described for formula I.

Another aspect of the invention provides a method for preventing inhibiting, or slowing the growth of L-cystine crystallization comprising administering an effective amount of a compound of formulae IIIa, IIIb, IIIc, IIId, or IIIe:

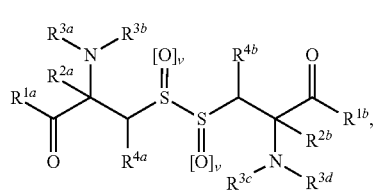   IIIa

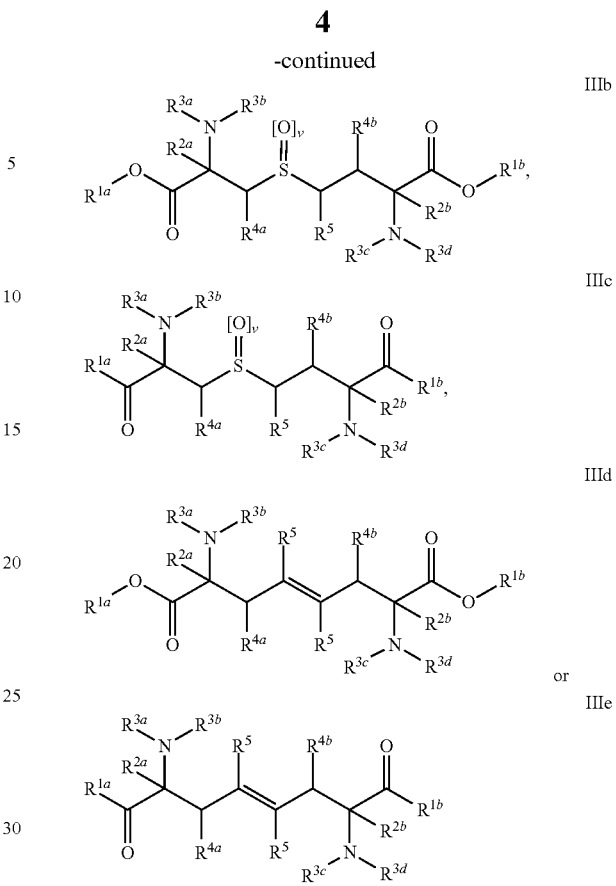

or a pharmaceutically acceptable salt, solvate, cocrystal, or prodrug thereof, and stereoisomers, tautomers and isotopic variants thereof; and wherein each $R^{1a}$ and $R^{1b}$ is independently selected from H, substituted or unsubstituted alkyl, substituted or unsubstituted aryl, substituted or unsubstituted aralkyl, and substituted or unsubstituted cycloalkyl;

each $R^{2a}$, $R^{2b}$, $R^{3a}$, $R^{3b}$, $R^{3c}$, $R^{3d}$, $R^{4a}$, $R^{4b}$, and $R^5$ is independently selected from H, substituted or unsubstituted alkyl, substituted or unsubstituted aryl, substituted or unsubstituted aralkyl, and substituted or unsubstituted cycloalkyl; and the subscript v is 0, 1, or 2.

In one particular embodiment of the invention, with respect to formula I and IIIa-IIIe, each of $R^{2a}$, $R^{2b}$, $R^{3a}$, $R^{3b}$, $R^{3c}$, $R^{3d}$, $R^{4a}$, $R^{4b}$, and $R^5$ is H.

In another particular embodiment of the invention, with respect to formula I and IIIa-IIIe, each of $R^{1a}$ and $R^{1b}$ is Me. In yet another embodiment, one of $R^{1a}$ and $R^{1b}$ is Me and the other is H.

In yet another particular embodiment of the invention, with respect to formula I, each n1 and n2 is 0.

Another aspect of the invention provides a method for preventing inhibiting, or slowing the growth of L-cystine crystallization comprising administering an effective amount of a compound of formulae XIIIa, XIIIb, XIIIc, or XIIId:

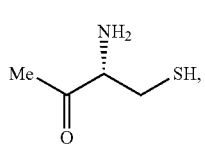   XIIIa

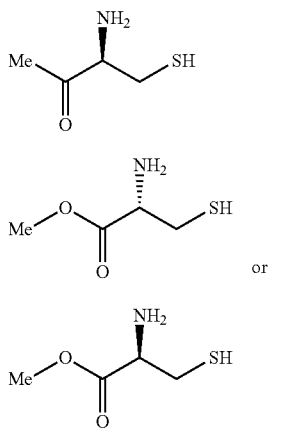

or a pharmaceutically acceptable salt, solvate, cocrystal, or prodrug thereof, and stereoisomers, tautomers and isotopic variants thereof.

Another aspect of the invention provides a pharmaceutical composition for preventing, inhibiting, or slowing the growth of L-cystine crystallization comprising a pharmaceutically acceptable carrier and a pharmaceutically effective amount of a compound according to formula I.

Yet another aspect of the invention provides a method for preventing, inhibiting or slowing growth of L-cystine kidney-stone formation in a subject in need thereof, the method comprising administering to the subject a pharmaceutically effective amount of a compound according to formula I.

Yet another aspect of the invention provides a method of treating a subject having chronic kidney disease, comprising administering to the subject a pharmaceutically effective amount of a compound according to formula I.

A further aspect of the invention provides a method for reducing a L-cystine crystal concentration in a human or animal comprising administering to a human or animal a pharmaceutically effective amount of a compound according to formula I.

A further aspect of the invention provides a method for treating an L-cystine crystal-related condition in a human or animal, comprising administering to a human or animal a pharmaceutically effective amount of a compound according to formula I.

A further aspect of the invention provides a combination to treat or prevent an L-cystine crystal-related condition, consisting of a compound according to formula I and another treatment or treatments, which may include high fluid intake or alkalinizing potassium or sodium salts.

In one embodiment, with respect to the above methods, the L-cystine related condition is cystinuria.

In one embodiment, with respect to the above methods, the L-cystine related condition is kidney stone disease.

In a further aspect, the present invention provides pharmaceutical compositions, comprising a compound or compounds of the invention, and a suitable biocompatible or bioinert carrier, excipient or diluent. In this aspect of the invention, pharmaceutical composition can comprise one or more of the compounds described herein. Moreover, the compounds of the present invention useful in pharmaceutical compositions and treatment methods disclosed herein, are all pharmaceutically acceptable as prepared and used.

In a further aspect, the present invention provides compositions comprising a combination of a compound of the invention with various compounds or agents that may have a like effect on L-cystine crystallization. In this aspect of the invention, the pharmaceutical composition can comprise one or more of the compounds described herein, individually or in combination with each other.

Other objects and advantages will become apparent to those skilled in the art from a consideration of the ensuing detailed description, which proceeds with reference to the following illustrative drawings.

DETAILED DESCRIPTION OF THE INVENTION

Definitions

Figure 1:
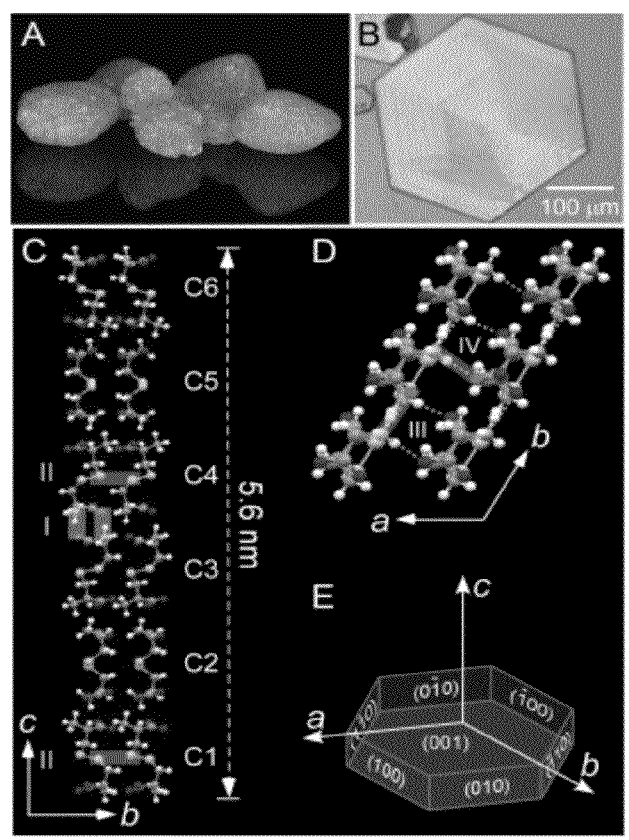
FIG. 1 depicts the hierarchical structure of L-cystine kidney stones, including the typical hexagonal platelet crystal habit formed in the absence of growth inhibitors. (A) Human stones with millimeter-scale dimensions (courtesy of M. Lewis, International Cystinuria Foundation). (B) A hexagonal L-cystine crystal prepared in vitro. The faint lines on the top surface of the crystal, parallel to the edges, are the {100} steps. (C) Two adjacent helices of L-cystine molecules, viewed on the (100) plane, each winding about a $6_1$ screw axis that coincides with the c axis. Six L-cystine molecules, denoted C1 to C6, span the 5.6 nm c axis. Key intermolecular interactions include amine-carboxylate hydrogen bonds along the helix (I, $d_{N...O}$=2.87 Å) and S...S interactions (II, $d_{S...S}$=3.47 Å) between helices at intervals of c/2, depicted here for C1 and C4 along the [010] direction (identical S...S interactions occur at symmetry-related sites along the other five equivalent directions). (D) Intermolecular amine-carboxylate hydrogen bonds in the (001) plane (III, $d_{N...O}$=2.79 Å; IV, $d_{N...O}$=2.81 Å). Atom color code: carbon (gray), oxygen (red), nitrogen (blue), sulfur (yellow), hydrogen (white). (E) Schematic illustration of a hexagonal L-cystine crystal, with Miller indices. The six planes flanking (001) belong to the {100} family.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

"Acyl" refers to a group or radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a group or radical —$NR^{21}C(O)R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group or radical —OC(O)$R^{23}$ where $R^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkoxy" refers to the group —$OR^{24}$ where $R^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —$NR^{25}C(O)R^{26}$ where $R^{25}$ is hydrogen, alkyl, aryl or cycloalkyl, and $R^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —N(H)$OR^{32}$ where $R^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —$NR^{33}R^{34}$ where $R^{33}$ represents an alkyl or cycloalkyl group and $R^{34}$ is an aryl as defined herein.

"Alkylsulfonyl" refers to a radical —S(O)$_2R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)$R^{35}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —$SR^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N($R^{36}$)$_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N($R^{36}$)$_2$ is an amino group.

"Aminocarbonyl" refers to the group —C(O)$NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}$C(O)$NR^{38}R^{38}$ where each $R^{38}$ is independently hydrogen, alkyl, aryl or cycloalkyl, or where two R groups are joined to form an alkylene group.

"Aminocarbonyloxy" refers to the group —OC(O)$NR^{39}R^{39}$ where each $R^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —$NHR^{40}$ where $R^{40}$ represents an aryl group as defined herein.

"Aryloxycarbonyl" refers to a radical —C(O)—O-aryl where aryl is as defined herein.

"Arylsulfonyl" refers to a radical —S(O)$_2R^{41}$ where $R^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N($R^{42}$)$_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$—P(O)(O$^-$)$_2$, —P(O)(OR$^{46}$)(O), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

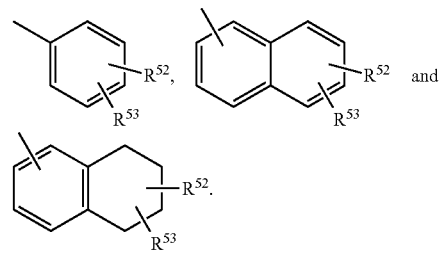

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

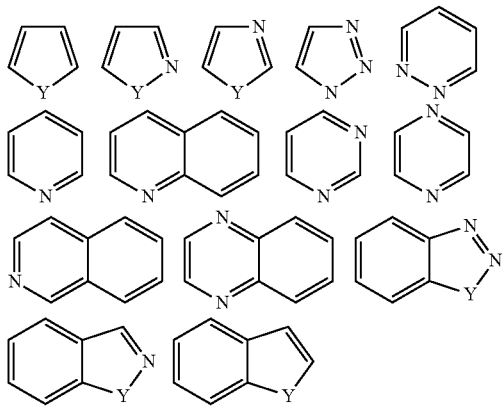

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

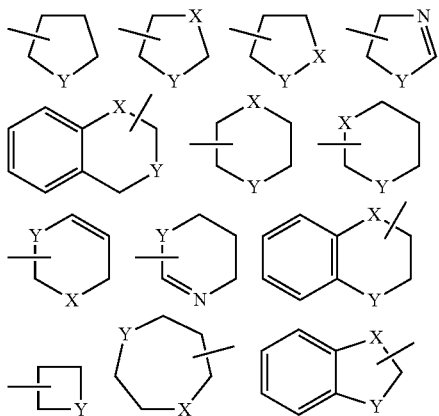

wherein each X is selected from $CR^{58}$, $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

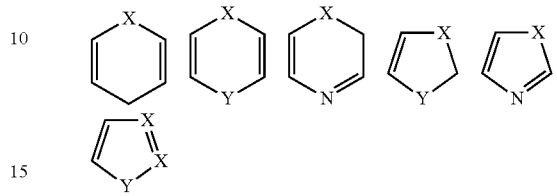

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

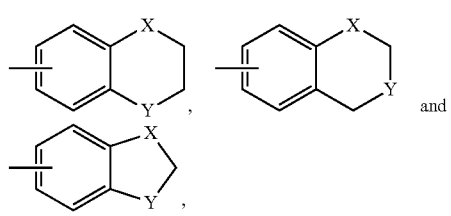

wherein each X is selected from $CR^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^4C$ group present as substituents directly on the ring or rings of the compounds of this invention, or that may be present as a substituent in any "substituted" aryl and aliphatic groups present in the compounds.

Examples of hetero substituents include:
-halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$)$_2$, —CONROR$^{59}$,
—SO$_3$H, —R$^{59}$—S, —SO$_2$N(R$^{59}$)$_2$,
—S(O)R$^{59}$, —S(O)$_2$R$^{59}$
wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as R$^{62}$$_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

As used herein, "mammal" refers to any member of the higher vertebrate animals comprising the class Mammalia, which includes, but is not limited to, humans.

As used herein, an "amount effective" shall mean an amount sufficient to cover the region of skin, hair, fur, or wool surface where a change in pigmentation is desired.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and/or that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease or a condition, is sufficient to effect such treatment for the disease or condition. The "therapeutically effective amount" can vary depending on the compound, the disease or condition and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or composition of the invention for cosmetic purposes.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

L-Cystine Stones and L-Cystine Crystalization

L-cystine stones are aggregates of individual crystals with hexagonal habits (FIG. 1). L-cystine can be crystallized in vitro at physiological pH (6≤pH≤8) by slow evaporation (a), acidification of basic L-cystine solutions to neutral pH (l), or gradual cooling of solutions supersaturated with L-cystine (a). Under these conditions, L-cystine crystallizes as hexagonal plates (FIG. 1B) with large (001) basal surfaces that can achieve widths of 400 nm and are bounded by six equivalent {100} faces. The typical thickness of these crystals ranges from 10-30 µm. The crystal structure (hexagonal P6$_1$22 space group, a=b=0.5422 nm, c=5.6275 nm) reveals L-cystine molecules organized as a helix about the 6$_1$ screw axis such that six cystine molecules span the ~5.6 nm unit cell length of the c-axis (a). The L-cystine molecules exhibit intermolecular $NH_3^+$ . . . $^-O(C=O)$ hydrogen bonding along the 6$_1$ screw axis (FIG. 1C, I), intermolecular S . . . S interactions between the helices at intervals of c/2 along each of the six equivalent {100} directions (FIG. 2C, II), and $NH_3^+$ . . . $^-O(C=O)$ hydrogen bonding (FIG. 1D, III, IV) between adjacent helices in the (001) plane. The hexagonal plate habit reflects the multiple strong intermolecular interactions in the (001) plane. The basal surfaces of L-cystine grown at neutral pH are decorated with {100} steps that are observable by either optical (FIG. 1B) or scanning electron microscopy, as described in Rimer, et al., Crystal Growth Inhibitors for the Prevention of L-Cystine Kidney Stones Through Molecular Design, *Science* 330, 337 (2010), expressly incorporated herein by reference in its entirety.

Crystal growth near equilibrium is commonly described by the terrace-ledge-kink model (c), wherein steps created by dislocations advance across crystal terraces by the addition of solute molecules to kink sites along the ledge (a ledge is the intersection of a step and terrace). Steps originating from screw dislocations typically exhibit a spiral growth pattern with the first turn occurring once each step has reached its critical length (c). Real-time in situ AFM of the L-cystine (001) face during growth in aqueous solutions containing L-cystine revealed steps emanating from screw dislocations, generating hexagonal hillocks in a spiral growth pattern.

Figure 2:
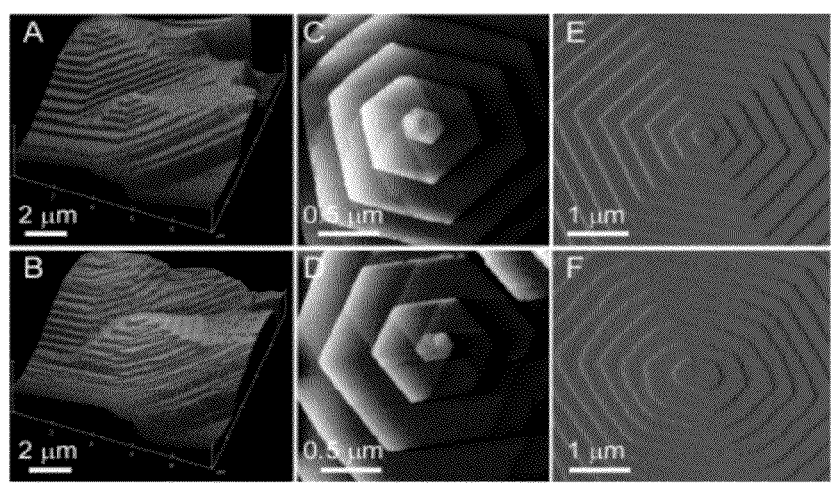
FIG. 2 depicts atomic force microscopy images of L-cystine crystal surface acquired in deflection mode.
(A,B) Real-time in situ AFM images of a L-cystine crystal, acquired 12 minutes apart. A pair of hexagonal hillocks generated by two closely spaced dislocations serve as landmarks. (C,D) AFM images of a single dislocation center of (C) L-cystine and (D) D-cystine crystal during growth. (E,F) AFM image of a hexagonal growth hillock on the (001) face of L-cystine before and after addition of an additive revealing roughening of the {100} steps due to step pinning Images were acquired in aqueous solutions containing 2 mM L-cystine.
Figure 3:
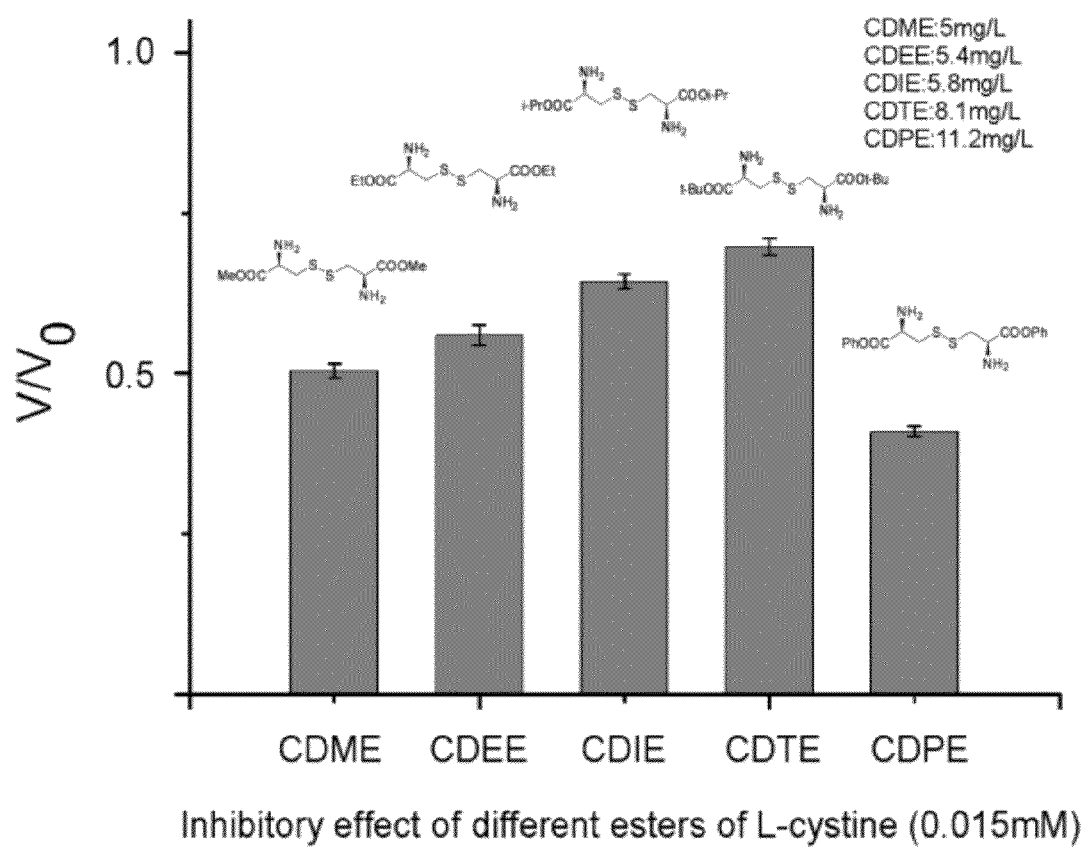
FIG. 3 depicts comparison of inhibitory effect of different diesters of L-Cystine (0.015 mM).
Figure 4:
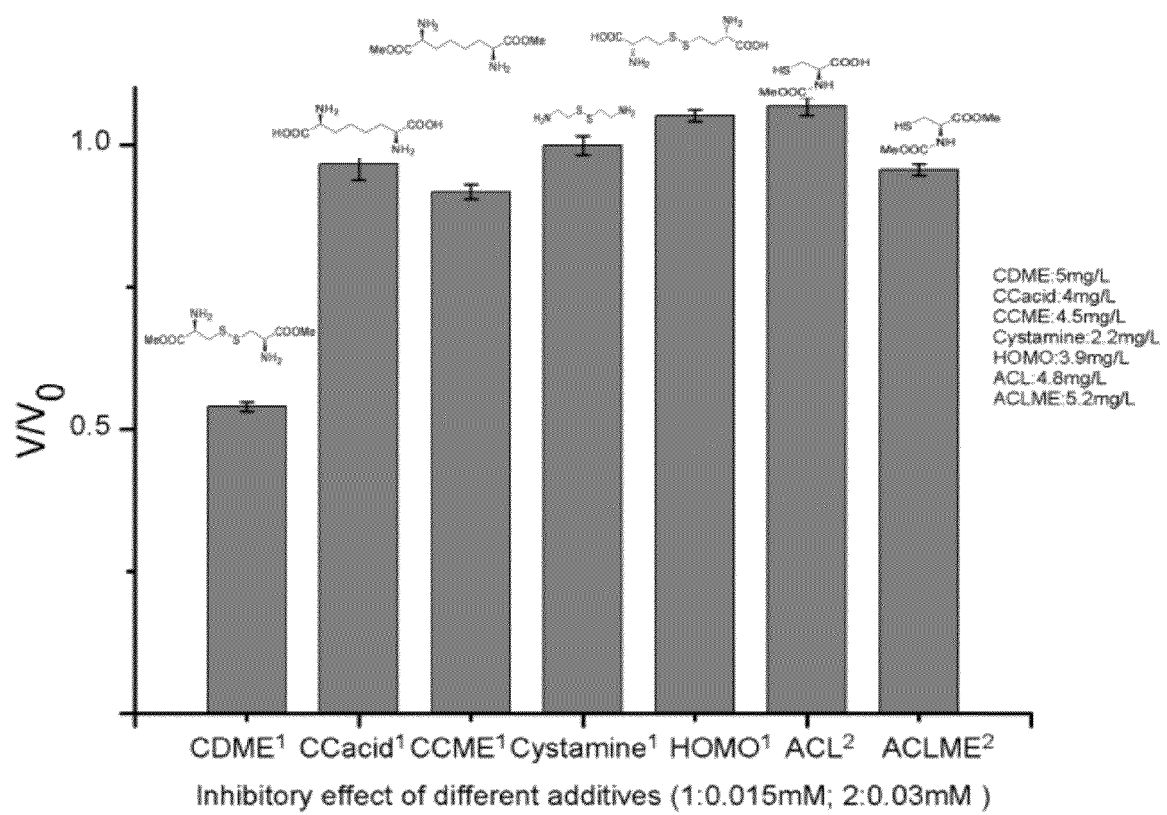
FIG. 4 depicts comparison of inhibitory effect of different additives.
Figure 5:
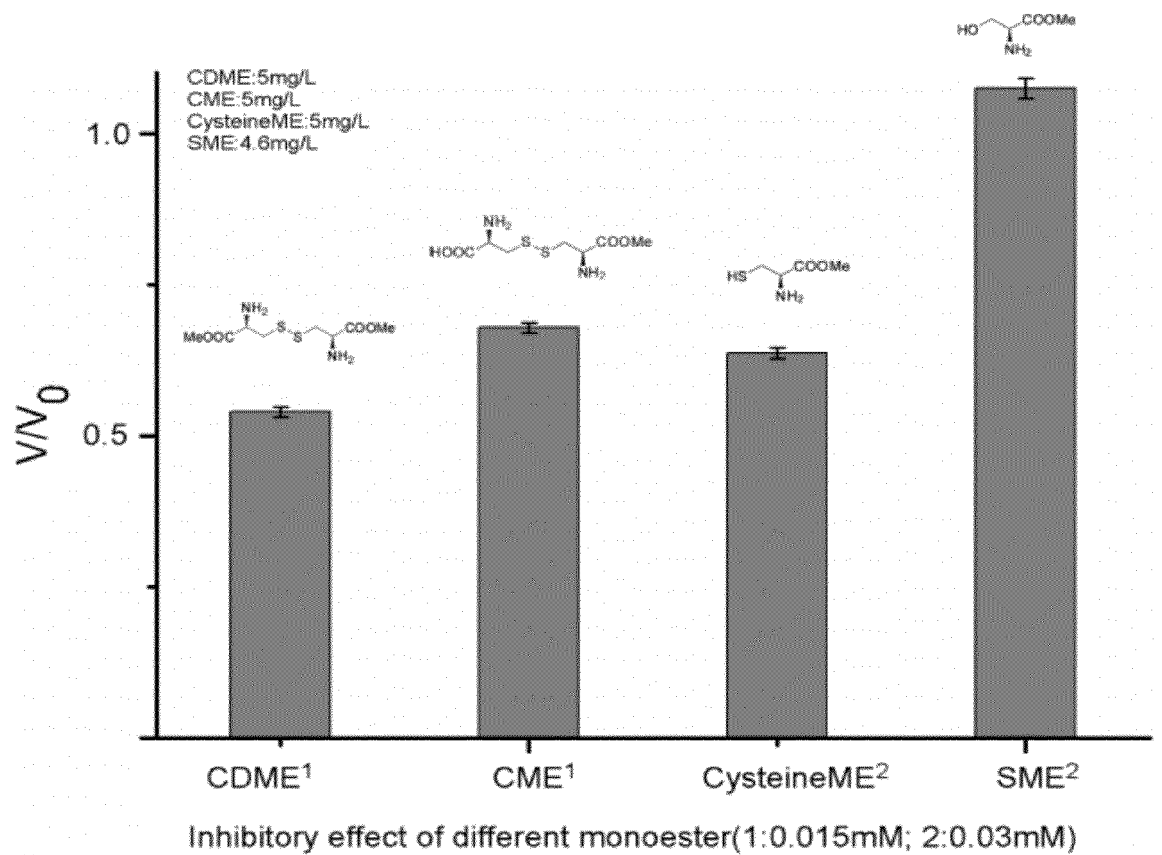
FIG. 5 depicts comparison of inhibitory effect of different monoesters of L-Cystine (0.015 mM and 0.03 mM).

Occasionally, multiple dislocations were observed (FIG. 2A,B), merging to generate a range of step heights from 1 nm to 60 nm, with the larger steps observed distant from the dislocation cores where step bunching would be expected. In contrast, hillocks generated by single isolated dislocations were bounded by six well-defined major {100} steps, each with a ~6 nm height corresponding to the unit cell length along c, separating (001) terraces. Each hillock terrace was decorated with six minor {100} steps at sixty degree intervals, each with a ~1 nm height corresponding to a single L-cystine molecule, creating the appearance of a pinwheel. These minor steps most likely reflect a splitting of the dislocation into six equivalent dislocations described by a Burgers vector having a magnitude of c/6. Consecutive images during crystal growth revealed a clockwise rotation of the pinwheel at the dislocation core (i.e. a left-handed screw) accompanied by continuous generation of new hillocks. Attachment of L-cystine molecules to both the minor and major steps on the surrounding terraces results in outward advancement of the steps with respect to the dislocation core (FIG. 2C). Notably, the spiral growth pattern also is observed for D-cystine, the unnatural enantiomer, but with counterclockwise (i.e. a right-handed screw) rotation of the pinwheel (FIG. 2D). A preference for screw dislocations of opposite handedness for enantiomeric crystals has been predicted (a).

The Compounds

As described herein, the present invention relates to the prevention of L-cystine kidney stones based on crystal growth inhibition via the binding of tailored growth inhibitors to specific crystal surfaces through molecular recognition. The compounds of the invention can be used to inhibit the rate of crystal growth, reduce crystal yield, and significantly alter crystal habit from hexagonal platelets to needles, suggesting a new strategy for the prevention of cystinuria.

Thus, one aspect of the invention provides a method for preventing inhibiting, or slowing the growth of L-cystine crystallization comprising administering an effective amount of a compound of formula I:

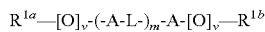

or a pharmaceutically acceptable salt, solvate, cocrystal, or prodrug thereof, and stereoisomers, tautomers and isotopic variants thereof; and wherein
each A is independently

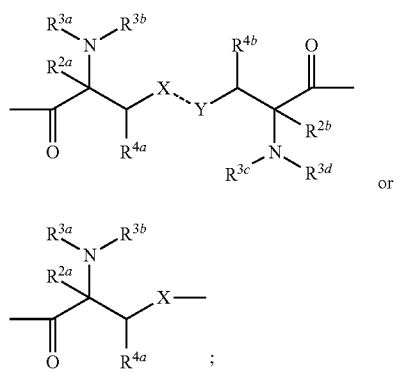

each X and Y is independently S, S(O), S(O)$_2$, or C(R$^5$)$_q$; each R$^{2a}$, R$^{2b}$, R$^{3a}$, R$^{3b}$, R$^{3c}$, R$^{3d}$, R$^{4a}$, R$^{4b}$, and R$^5$ is independently selected from H, substituted or unsubstituted alkyl, substituted or unsubstituted aryl, substituted or unsubstituted aralkyl, and substituted or unsubstituted cycloalkyl; the subscript q is 1 or 2;

the dotted bond is a single or a double bond;

provided that when one of X and Y is S, S(O), or S(O)$_2$, then the dotted bond is a single bond;

L is —O—C$_1$-C$_6$ alkylene-O—, —O-aryl-O—, or a group —O—(CH$_2$—CH$_2$—O—)$_t$—; the subscript t is 1-10; the subscript m is 0-10;

each R$^{1a}$ and R$^{1b}$ is independently selected from H, substituted or unsubstituted alkyl, substituted or unsubstituted aryl, substituted or unsubstituted aralkyl, and substituted or unsubstituted cycloalkyl; and each subscript v is 0 or 1.

In one particular embodiment, with respect to formula I, when A is Ia', both X and Y are S, S(O), or S(O)$_2$, and m is 0, then each subscript v is 0.

In one particular aspect of the invention provides a method for preventing inhibiting, or slowing the growth of L-cystine crystallization comprising administering an effective amount of a compound of formula I or a pharmaceutically acceptable salt, solvate, cocrystal, or prodrug thereof, and stereoisomers, tautomers and isotopic variants thereof; and the formula I is as described above, provided that when A is Ia', both X and Y are S, S(O), or S(O)$_2$, and m is 0, then each subscript v is 0.

In one embodiment, the present invention excludes compounds according to formula I, wherein A is Ia', both X and Y are S, S(O), or S(O)$_2$, m is 0, each subscript v is 1, and each R$^{1a}$ and R$^{1b}$ is independently H, Me, Et, i-Pr or t-Bu.

In one particular embodiment, with respect to formula I, when A is Ia', both X and Y are S, S(O), or S(O)$_2$, and m is 0, each subscript v is 1; then at least one of R$^{1a}$ and R$^{1b}$ is substituted or unsubstituted Ph. One particular embodiment, each of R$^{1a}$ and R$^{1b}$ is substituted or unsubstituted Ph. One particular embodiment, each of R$^{1a}$ and R$^{1b}$ is unsubstituted Ph.

In one embodiment, with respect to formula I, A is

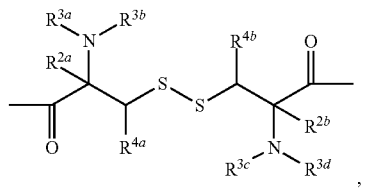

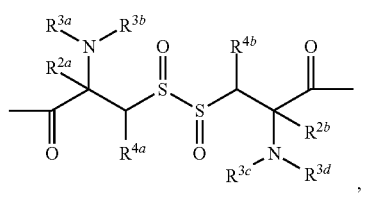

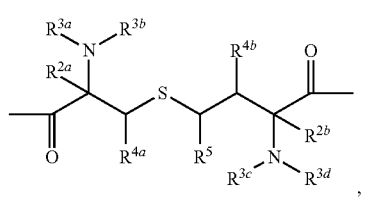

-continued

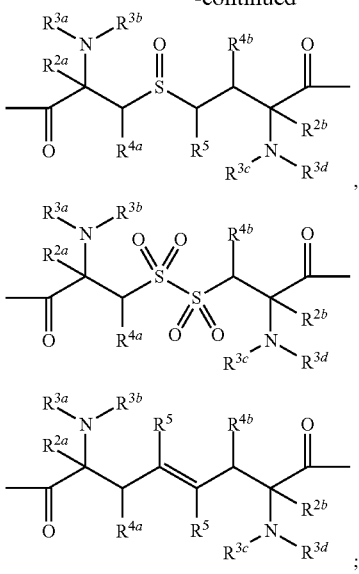

and wherein $R^{2a}$, $R^{2b}$, $R^{3a}$, $R^{3b}$, $R^{3c}$, $R^{3d}$, $R^{4a}$, $R^{4b}$, and $R^5$ are as described for formula I.

In one embodiment, with respect to formula I, the subscript m is 1-5.

In one embodiment, with respect to formula I, L is —O—CH$_2$—O—. In another embodiment L is —O—CH$_2$—CH$_2$—O—.

In one embodiment, with respect to formula I, L is

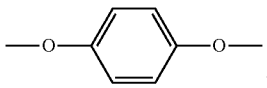

In one embodiment, with respect to formula I, L is —O—(CH$_2$—CH$_2$—O)$_t$—; and the subscript t is 1; In another embodiment the subscript t is 2.

In one embodiment, with respect to formula I, subscript m is 0; and the subscript v is 0.

In one embodiment, with respect to formula I, subscript m is 0; and the compound is according to formula II:

    II and wherein A, $R^{1a}$ and $R^{1b}$ are as described for formula I.

Another aspect of the invention provides a method for preventing, inhibiting or slowing the growth of L-cystine crystallization comprising administering an effective amount of a compound of formulae IIIa, IIIb, IIIc, IIId, or IIIe:

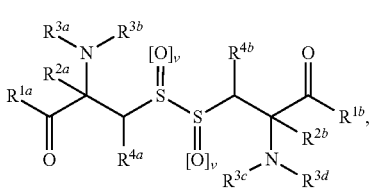    IIIa

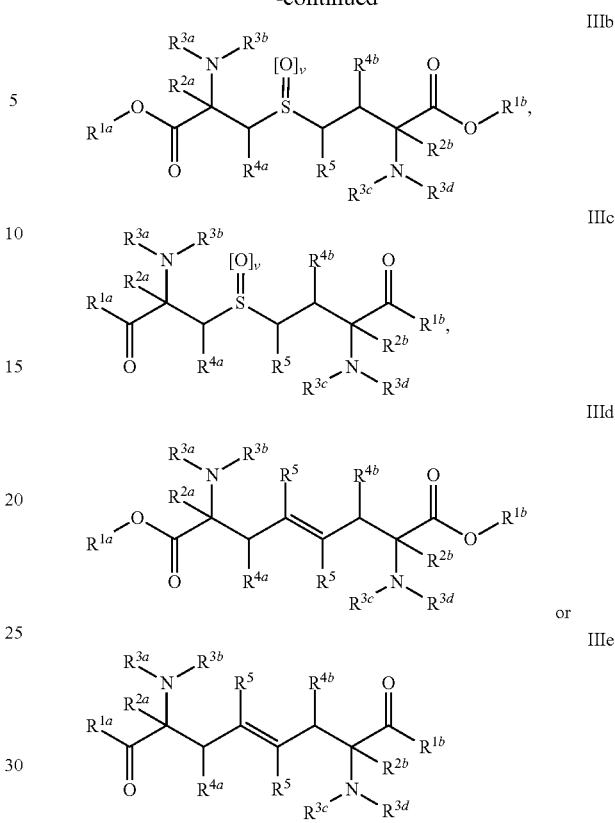

or a pharmaceutically acceptable salt, solvate, cocrystal, or prodrug thereof, and stereoisomers, tautomers and isotopic variants thereof; and wherein each $R^{1a}$ and $R^{1b}$ is independently selected from H, substituted or unsubstituted alkyl, substituted or unsubstituted aryl, substituted or unsubstituted aralkyl, and substituted or unsubstituted cycloalkyl;

each $R^{2a}$, $R^{2b}$, $R^{3a}$, $R^{3b}$, $R^{3c}$, $R^{3d}$, $R^{4a}$, $R^{4b}$, and $R^5$ is independently selected from H, substituted or unsubstituted alkyl, substituted or unsubstituted aryl, substituted or unsubstituted aralkyl, and substituted or unsubstituted cycloalkyl; and the subscript v is 0, 1, or 2.

In one embodiment of the invention, with respect to formula I, II, or IIIa-IIIe, each $R^{2a}$, $R^{2b}$, $R^{3a}$, $R^{3b}$, $R^{3c}$, $R^{3d}$, $R^{4a}$, $R^{4b}$, and $R^5$ is independently H or alkyl.

In one embodiment of the invention, with respect to formula I, II, or IIIa-IIIe, each of $R^{4a}$ and $R^{4b}$ is H.

In another embodiment of the invention, with respect to formula I, II, or IIIa-IIIe, one of $R^{4a}$ and $R^{4b}$ is H; and the other is alkyl.

In another embodiment of the invention, with respect to formula I, II, or IIIa-IIIc, one of $R^{4a}$ and $R^{4b}$ is H; and the other is Me, Et, i-Pr, n-Pr, or n-Bu.

In another embodiment of the invention, with respect to formula I, II, or IIIa-IIIe, each of $R^{4a}$ and $R^{4b}$ is alkyl.

In another embodiment of the invention, with respect to formula I, II, or IIIa-IIIe, each of $R^{4a}$ and $R^{4b}$ is Me, Et, i-Pr, n-Pr, or n-Bu.

In another embodiment of the invention, with respect to formula I, II, or IIIa-IIIe, each of $R^{4a}$ and $R^{4b}$ is Me.

In another embodiment of the invention, with respect to formula I, II, or IIIa-IIIe, one of $R^5$ is H; and the other is Me, Et, i-Pr, n-Pr, or n-Bu.

In another embodiment of the invention, with respect to formula I, II, or IIIa-IIIe, each $R^5$ is alkyl.

In another embodiment of the invention, with respect to formula I, II, or IIIa-IIIe, each $R^5$ is H.

In one embodiment of the invention, with respect to formula I, II, or IIIa-IIIe, $R^{4b}$, and $R^5$ is independently selected from H, and alkyl.

In one embodiment of the invention, with respect to formula I, II, or IIIa-IIIe, each of $R^{2a}$ and $R^{2b}$ is H.

In another embodiment of the invention, with respect to formula I, II, or IIIa-IIIe, one of $R^{2a}$ and $R^{2b}$ is H; and the other is alkyl.

In another embodiment of the invention, with respect to formula I, II, or IIIa-IIIe, one of $R^{2a}$ and $R^{2b}$ is H; and the other is independently Me, Et, i-Pr, n-Pr, or n-Bu.

In another embodiment of the invention, with respect to formula I, II, or IIIa-IIIe, each of $R^{2a}$ and $R^{2b}$ is alkyl.

In another embodiment of the invention, with respect to formula I, II, or IIIa-IIIe, each of $R^{2a}$ and $R^{2b}$ is independently Me, Et, i-Pr, n-Pr, or n-Bu.

In one particular embodiment of the invention, with respect to formula I, II, or IIIa-IIIe, each of $R^{2a}$ and $R^{2b}$ is Me.

In one embodiment of the invention, with respect to formula I, II, or IIIa-IIIe, each of $R^{3c}$ and $R^{3d}$ is H.

In another embodiment of the invention, with respect to formula I, II, or IIIa-IIIe, one of $R^{3c}$ and $R^{3d}$ is H; and the other is alkyl.

In another embodiment of the invention, with respect to formula I, II, or IIIa-IIIe, one of $R^{3c}$ and $R^{3d}$ is H; and the other is independently Me, Et, i-Pr, n-Pr, or n-Bu.

In another embodiment of the invention, with respect to formula I, II, or IIIa-IIIe, each of $R^{3c}$ and $R^{3d}$ is alkyl.

In another embodiment of the invention, with respect to formula I, II, or IIIa-IIIe, each of $R^{3c}$ and $R^{3d}$ is independently Me, Et, i-Pr, n-Pr, or n-Bu.

In another embodiment of the invention, with respect to formula I, II, or IIIa-IIIe, each of $R^{3c}$ and $R^{3d}$ is Me.

Another aspect of the invention provides a method for preventing, inhibiting or slowing the growth of L-cystine crystallization comprising administering an effective amount of a compound of formulae IIIf, or IIIg:

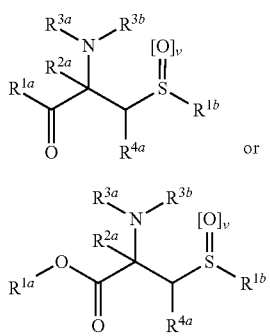

or a pharmaceutically acceptable salt, solvate, cocrystal, or prodrug thereof, and stereoisomers, tautomers and isotopic variants thereof; and wherein each $R^{1a}$ and $R^{1b}$ is independently selected from H, alkyl, alkenyl, alkynyl, aryl, aralkyl, and cycloalkyl;

each $R^{2a}$, $R^{2b}$, $R^{3a}$, $R^{3b}$, $R^{3c}$, $R^{3d}$, and $R^{4a}$ is independently selected from H, substituted or unsubstituted alkyl, substituted or unsubstituted aryl, substituted or unsubstituted aralkyl, and substituted or unsubstituted cycloalkyl; and the subscript v is 0, 1, or 2.

In one embodiment of the invention, with respect to formula I, II, or IIIa-IIIg, $R^{2a}$, $R^{2b}$, $R^{3a}$, $R^{3b}$, $R^{3c}$, $R^{3d}$, and $R^{4a}$ is independently selected from H, and alkyl.

In one embodiment of the invention, with respect to formula I, II, or IIIa-IIIg, $R^{4a}$ is H.

In one embodiment of the invention, with respect to formula I, II, or IIIa-IIIg, $R^{4a}$ is alkyl.

In one embodiment of the invention, with respect to formula I, II, or IIIa-IIIg, $R^{4a}$ is Me, Et, i-Pr, n-Pr, or n-Bu.

In one embodiment of the invention, with respect to formula I, II, or IIIa-IIIg, $R^{2a}$ is H.

In one embodiment of the invention, with respect to formula I, II, or IIIa-IIIg, $R^{2a}$ is alkyl.

In one embodiment of the invention, with respect to formula I, II, or IIIa-IIIg, $R^{2a}$ is Me, Et, i-Pr, n-Pr, or n-Bu.

In one embodiment of the invention, with respect to formula I, II, or IIIa-IIIg, each of $R^{3a}$ and $R^{3b}$ is H.

In another embodiment of the invention, with respect to formula I, II, or IIIa-IIIg, one of $R^{3a}$ and $R^{3b}$ is H; and the other is alkyl.

In one embodiment of the invention, with respect to formula I, II, or IIIa-IIIg, one of $R^{3a}$ and $R^{3b}$ is H; and the other is independently Me, Et, i-Pr, n-Pr, or n-Bu.

In another embodiment of the invention, with respect to formula I, II, or IIIa-IIIg, each of $R^{3a}$ and $R^{3b}$ is alkyl.

In another embodiment of the invention, with respect to formula I, II, or IIIa-IIIg, each of $R^{3a}$ and $R^{3b}$ is independently Me, Et, i-Pr, n-Pr, or n-Bu.

In another embodiment of the invention, with respect to formula I, II, or IIIa-IIIg, each of $R^{3a}$ and $R^{3b}$ is Me.

In one embodiment of the invention, with respect to formula I, the compound is according to formula IVa, IVb, IVc or IVd:

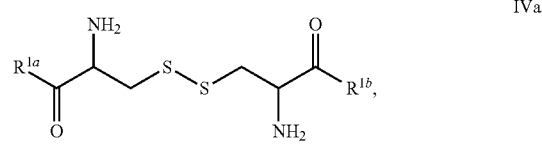

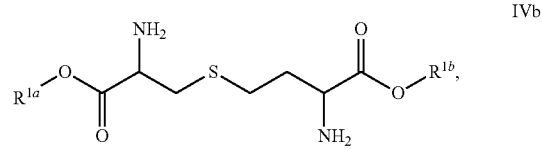

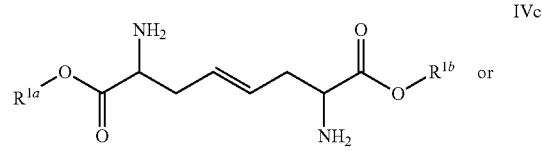

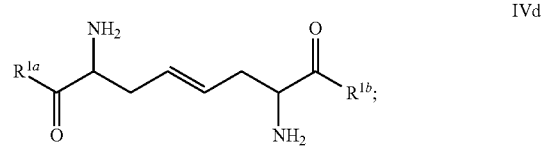

and wherein $R^{1a}$ and $R^{1b}$ are as with respect to formula I; or a pharmaceutically acceptable salt, solvate, cocrystal, or prodrug thereof, and stereoisomers, tautomers and isotopic variants thereof.

In one embodiment of the invention, with respect to formula I, the compound is according to formula IVe, or IVf:

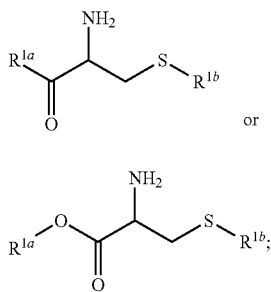

IVe

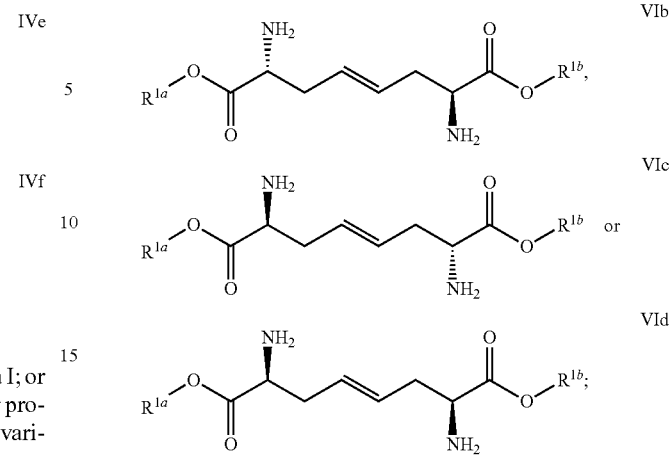

VIb

VIc

VId and wherein $R^{1a}$ and $R^{1b}$ are as with respect to formula I; or a pharmaceutically acceptable salt, solvate, cocrystal, or prodrug thereof, and stereoisomers, tautomers and isotopic variants thereof.

IVf and wherein $R^{1a}$ and $R^{1b}$ are as with respect to formula I; or a pharmaceutically acceptable salt, solvate, cocrystal, or prodrug thereof, and stereoisomers, tautomers and isotopic variants thereof.

In one particular embodiment of the invention, with respect to formula I, the compound is according to formula Va, Vb, Vc, or Vd:

In one particular embodiment of the invention, with respect to formula I, the compound is according to formula VIIa, VIIb, VIIc, or VIId:

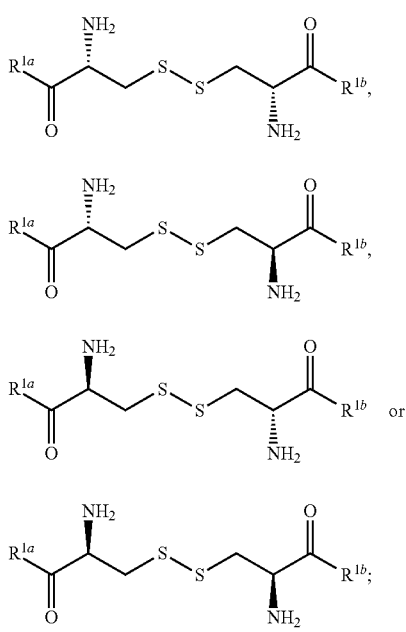

Va

Vb

Vc

Vd

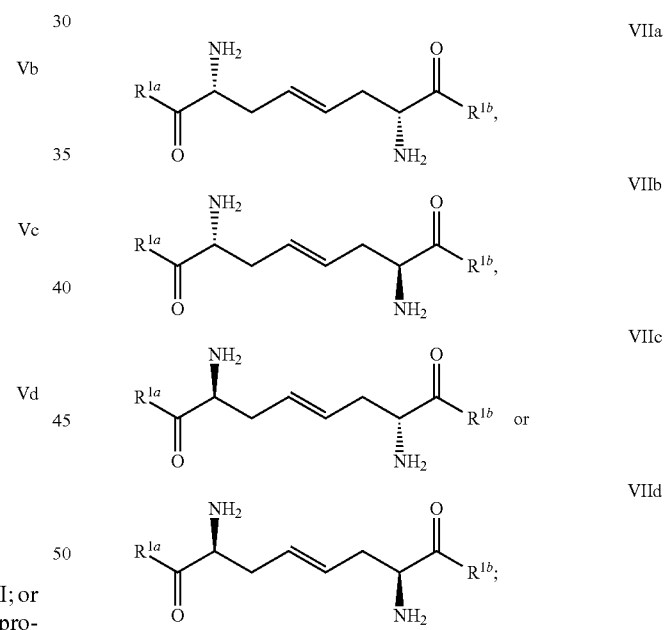

VIIa

VIIb

VIIc

VIId and wherein $R^{1a}$ and $R^{1b}$ are as with respect to formula I; or a pharmaceutically acceptable salt, solvate, cocrystal, or prodrug thereof, and stereoisomers, tautomers and isotopic variants thereof.

In one embodiment of the invention, with respect to formula I, the compound is according to formula VIa, VIb, VIc, or VId:

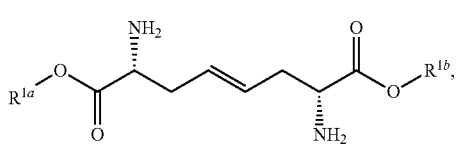

VIa and wherein $R^{1a}$ and $R^{1b}$ are as with respect to formula I; or a pharmaceutically acceptable salt, solvate, cocrystal, or prodrug thereof, and stereoisomers, tautomers and isotopic variants thereof.

In one embodiment of the invention, with respect to formula I-VIId, one of $R^{1a}$ and $R^{1b}$ is H; and the other is alkyl.

In another embodiment of the invention, with respect to formula I-VIId, one of $R^{1a}$ and $R^{1b}$ is H; and the other is independently Me, Et, n-Pr, i-Pr, n-Bu, or t-Bu.

In another embodiment of the invention, with respect to formula I-VIId, one of $R^{1a}$ and $R^{1b}$ is H; and the other is alkenyl.

T In another embodiment of the invention, with respect to formula I-VIId, one of $R^{1a}$ and $R^{1b}$ is H; and the other is alkynyl.

In another embodiment of the invention, with respect to formula I-VIId, one of $R^{1a}$ and $R^{1b}$ is H; and the other is propargyl.

In another embodiment of the invention, with respect to formula I-VIId, one of $R^{1a}$ and $R^{1b}$ is H; and the other is cycloalkyl.

In another embodiment of the invention, with respect to formula I-VIId, one of $R^{1a}$ and $R^{1b}$ is H; and the other is cyclohexyl, cyclopentyl, cyclobutyl, or cyclopropyl.

In another embodiment of the invention, with respect to formula I-VIId, one of $R^{1a}$ and $R^{1b}$ is H; and the other is Me, Et, or cyclopropyl.

In another embodiment of the invention, with respect to formula I-VIId, each of $R^{1a}$ and $R^{1b}$ is alkyl.

In another embodiment of the invention, with respect to formula I-VIId, each of $R^{1a}$ and $R^{1b}$ is independently Me, Et, n-Pr, i-Pr, n-Bu, or t-Bu.

In another embodiment of the invention, with respect to formula I-VIId, each of $R^{1a}$ and $R^{1b}$ is alkenyl.

In another embodiment of the invention, with respect to formula I-VIId, each of $R^{1a}$ and $R^{1b}$ is alkynyl.

In another embodiment of the invention, with respect to formula I-VIId, each of $R^{1a}$ and $R^{1b}$ is propargyl.

In another embodiment of the invention, with respect to formula I-VIId, each of $R^{1a}$ and $R^{1b}$ is cycloalkyl.

In another embodiment of the invention, with respect to formula I-VIId, each of $R^{1a}$ and $R^{1b}$ is independently cyclohexyl, cyclopentyl, cyclobutyl, or cyclopropyl.

In another embodiment of the invention, with respect to formula I-VIId, each of $R^{1a}$ and $R^{1b}$ is independently Me, Et, or cyclopropyl.

In one particular embodiment of the invention, with respect to formula I-VIId, each of $R^{1a}$ and $R^{1b}$ is Me.

In one particular embodiment of the invention, with respect to formula I-VIId, each of $R^{1a}$ and $R^{1b}$ is substituted or unsubstituted Ph.

Another aspect of the invention provides a method for preventing, inhibiting or slowing the growth of L-cystine crystallization comprising administering an effective amount of cystamine.

In one embodiment of the invention, with respect to formula I, the compound is according to formula VIIIa or VIIIb:

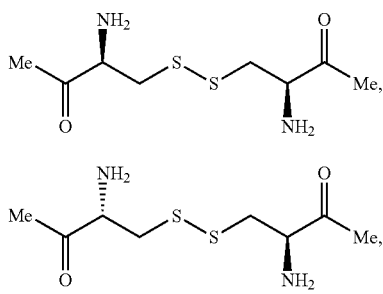

or a pharmaceutically acceptable salt, solvate, cocrystal, or prodrug thereof, and stereoisomers, tautomers and isotopic variants thereof.

In one embodiment of the invention, with respect to formula I, the compound is according to formula IXa, or IXb:

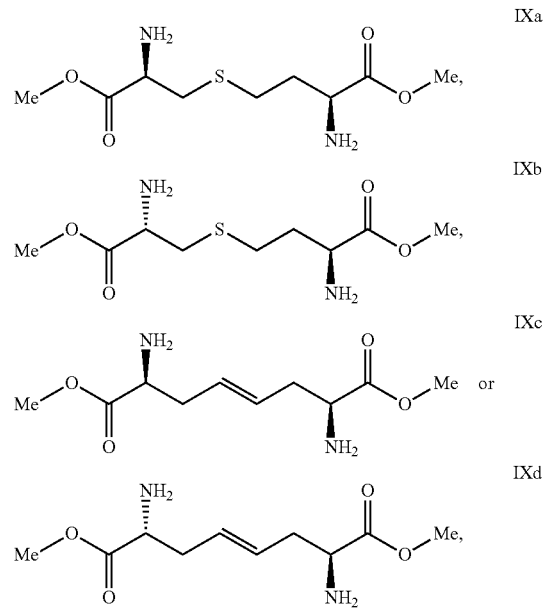

or a pharmaceutically acceptable salt, solvate, cocrystal, or prodrug thereof, and stereoisomers, tautomers and isotopic variants thereof.

In one particular embodiment of the invention, with respect to formula I, the compound is according to formula Xa or Xb:

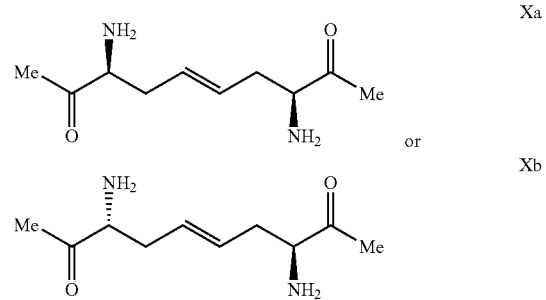

or a pharmaceutically acceptable salt, solvate, cocrystal, or prodrug thereof, and stereoisomers, tautomers and isotopic variants thereof.

In one particular embodiment of the invention, with respect to formula I, the compound is according to formula XI:

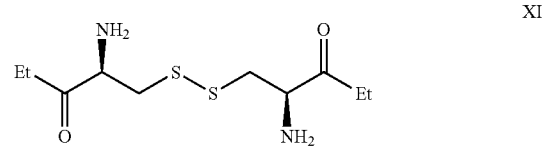 [SMILES: CCC(=O)[C@@H](N)CSSC[C@H](N)C(=O)CC]

or a pharmaceutically acceptable salt, solvate, cocrystal, or prodrug thereof, and stereoisomers, tautomers and isotopic variants thereof.

In one particular embodiment of the invention, with respect to formula I, the compound is according to formula XIIa, XIIb, XIIc, or XIId:

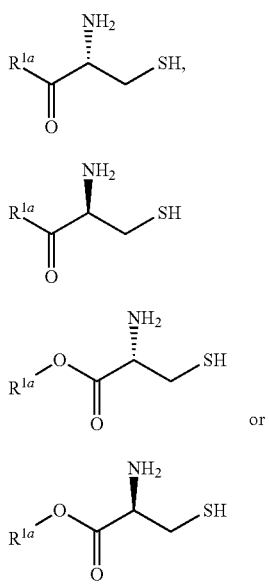

or a pharmaceutically acceptable salt, solvate, cocrystal, or prodrug thereof, and stereoisomers, tautomers and isotopic variants thereof.

In one embodiment of the invention, with respect to formula XIIa-XIId, $R^{1a}$ is substituted or unsubstituted alkyl, substituted or unsubstituted aryl, substituted or unsubstituted aralkyl, or substituted or unsubstituted cycloalkyl.

In one embodiment of the invention, with respect to formula XIIa-XIId, $R^{1a}$ is alkenyl.

In one embodiment of the invention, with respect to formula XIIa-XIId, $R^{1a}$ is alkynyl.

In one embodiment of the invention, with respect to formula XIIa-XIId, $R^{1a}$ is propargyl.

In one embodiment of the invention, with respect to formula XIIa-XIId, $R^{1a}$ is cycloalkyl.

In one embodiment of the invention, with respect to formula XIIa-XIId, $R^{1a}$ is cyclohexyl, cyclopentyl, cyclobutyl, or cyclopropyl.

In one embodiment of the invention, with respect to formula XIIa-XIId, $R^{1a}$ is Me, Et, n-Pr, i-Pr, n-Bu, t-Bu, or Ph.

In one embodiment of the invention, with respect to formula XIIa-XIId, $R^{1a}$ is substituted or unsubstituted Ph.

In one particular embodiment of the invention, with respect to formula I, the compound is according to formula XIIIa, XIIIb, XIIIc, or XIIId:

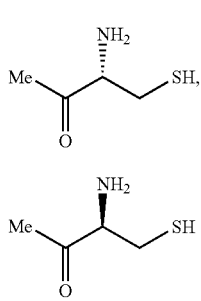

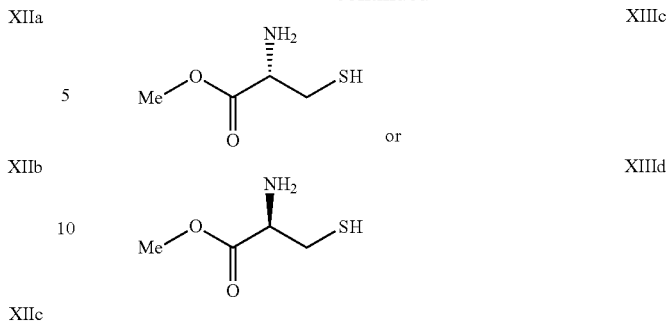

or a pharmaceutically acceptable salt, solvate, cocrystal, or prodrug thereof, and stereoisomers, tautomers and isotopic variants thereof.

In one particular embodiment of the invention, with respect to formula I, the compound is according to formula XIVa, XIVb, XIVc, or XIVd:

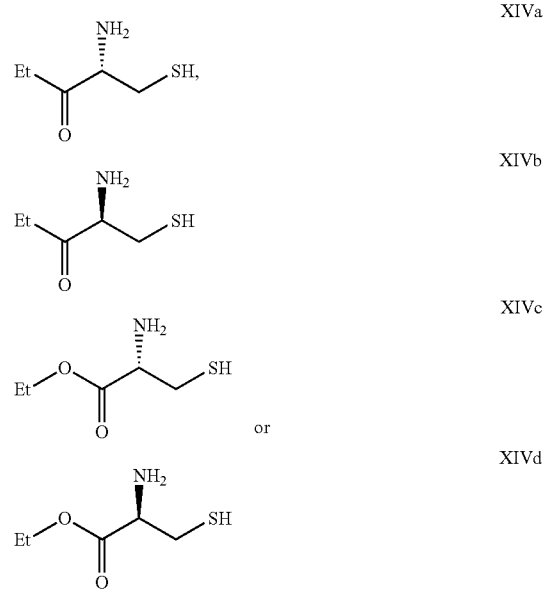

or a pharmaceutically acceptable salt, solvate, cocrystal, or prodrug thereof, and stereoisomers, tautomers and isotopic variants thereof.

In one particular embodiment of the invention, with respect to formula I, the compound is according to formula XVa, XVb, XVc, or XVd:

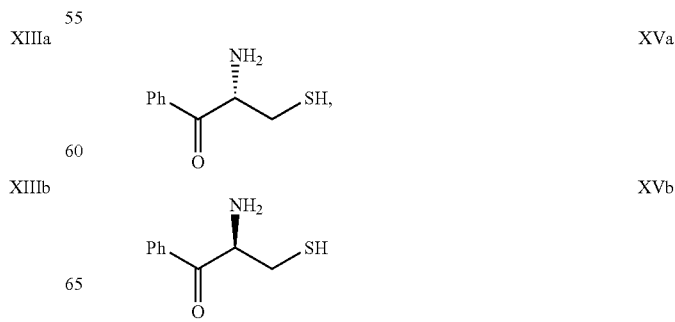

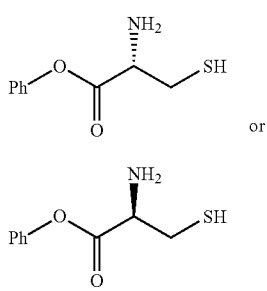

XVc or

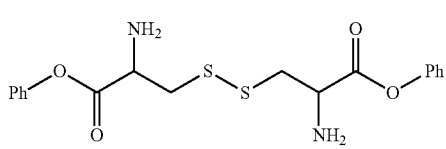

XVd or a pharmaceutically acceptable salt, solvate, cocrystal, or prodrug thereof, and stereoisomers, tautomers and isotopic variants thereof.

In one embodiment of the invention, with respect to formula I, the compound is according to formula XVI:

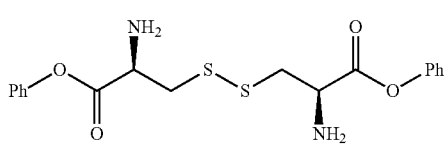

XVI or a pharmaceutically acceptable salt, solvate, cocrystal, or prodrug thereof, and stereoisomers, tautomers and isotopic variants thereof.

In one embodiment of the invention, with respect to formula I, the compound is according to formula XVII:

XVII or a pharmaceutically acceptable salt, solvate, cocrystal, or prodrug thereof, and stereoisomers, tautomers and isotopic variants thereof.

In one particular embodiment of the invention, with respect to formula XVa-XVd, XVI, and XVII, Ph is unstituted. In another embodiment Ph is substituted. In a particular embodiment, Ph is substituted with alkyl, haloalkyl, alkoxy, or halo.

In one particular embodiment of the invention, with respect to formula I, the compound is any one of the compounds listed in Table 1.

In one particular embodiment of the invention, with respect to formula I, the compound is any one of the compounds listed in Table 1, and wherein the compound # is 2, 3, 9, 10, 12, or 14.

In one particular embodiment of the invention, with respect to formula I, the compound is any one of the compounds listed in Table 1, and wherein the compound # is 2.

In one particular embodiment of the invention, with respect to formula I, the compound is L-cysteine methyl ester.

In one particular embodiment of the invention, with respect to formula I, the compound is L-homocystine dimethyl ester.

In one particular embodiment of the invention, with respect to formula I, the compound is L-dimethyl 2,7-diamino oct-4-enedioate.

In one particular embodiment of the invention, with respect to formula I, the compound is L-dimethyl 2,7-diamino octanedioate.

In one particular embodiment of the invention, with respect to formula I, the compound is N-acetyl-L-cysteine methyl ester.

In one particular embodiment of the invention, with respect to formula I, the compound is L-diaminooctanedioic acid.

In one particular embodiment of the invention, with respect to formula I, N-acetyl-L-cysteine.

In one particular embodiment of the invention, with respect to formula I, the compound is L-serine methyl ester.

In one particular embodiment of the invention, with respect to formula I, the compound is L-cystine diphenyl ester.

Another aspect of the invention provides a pharmaceutical composition for preventing, inhibiting, or slowing the growth of L-cystine crystallization comprising a pharmaceutically acceptable carrier and a pharmaceutically effective amount of a compound according to formula I, II, IIIa-IIIg, IVa-IVd, Va-Vd, VIa-VIId, VIIa-VIId, VIIIa-VIIIb, IXa-IXd, Xa-Xb, XI, XIIa-XIId, XIIIa-XIIId, XIVa-XIVd, XVa-XVd, XVI or XVII.

Yet another aspect of the invention provides a method for preventing, inhibiting or slowing growth of L-cystine kidney-stone formation in a subject in need thereof, the method comprising administering to the subject a pharmaceutically effective amount of a compound according to formula I, II, IIIa-IIIg, IVa-IVd, Va-Vd, VIa-VIId, VIIa-VIId, VIIIa-VIIIb, IXa-IXd, Xa-Xb, XI, XIIa-XIId, XIIIa-XIIId, XIVa-XIVd, XVa-XVd, XVI or XVII.

Yet another aspect of the invention provides a method of treating a subject having chronic kidney disease, comprising administering to the subject a pharmaceutically effective amount of a compound according to formula I, II, IIIa-IIIg, IVa-IVd, Va-Vd, VIa-VIId, VIIa-VIId, VIIIa-VIIIb, IXa-IXd, Xa-Xb, XI, XIIa-XIId, XIIIa-XIIId, XIVa-XIVd, XVa-XVd, XVI or XVII.

In one embodiment, with respect to the above methods, the subject is human.

A further aspect of the invention provides a method for reducing a L-cystine crystal concentration in a human or animal comprising administering to a human or animal a pharmaceutically effective amount of a compound according to formula I, II, IIIa-IIIg, IVa-IVd, Va-Vd, VIa-VIId, VIIa-VIId, VIIIa-VIIIb, IXa-IXd, Xa-Xb, XI, XIIa-XIId, XIIIa-XIIId, XIVa-XIVd, XVa-XVd, XVI or XVII.

A further aspect of the invention provides a method for treating a L-cystine crystal related condition in a human or animal comprising administering to a human or animal a pharmaceutically effective amount of a compound according to formula I, II, IIIa-IIIg, IVa-IVd, Va-Vd, VIa-VIId, VIIa-VIId, VIIIa-VIIIb, IXa-IXd, Xa-Xb, XI, XIIa-XIId, XIIIa-XIIId, XIVa-XIVd, XVa-XVd, XVI or XVII.

A further aspect of the invention provides a combination to treat or prevent an L-cystine crystal-related condition consisting of a compound according to formula I, II, IIIa-IIIg, IVa-IVd, Va-Vd, VIa-VIId, VIIa-VIId, VIIIa-VIIIb, IXa-IXd, Xa-Xb, XI, XIIa-XIId, XIIIa-XIIId, XIVa-XIVd, XVa-XVd, XVI or XVII, and another treatment or treatments, which may include high fluid intake or alkalinizing potassium or sodium salts.

In one embodiment, with respect to the above methods, the L-cystine related condition is cystinuria.

In one embodiment, with respect to the above methods, the L-cystine related condition is kidney stone disease.

In certain aspects, the present invention provides prodrugs and derivatives of the compounds of the invention. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

The present invention also relates to the pharmaceutically acceptable acid addition and base salts of any of the aforementioned compounds of invention. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful according to the invention that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds useful according to the invention that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description, examples, and the claims.

Pharmaceutical Applications

For pharmaceutical uses, it is preferred that the compounds of the invention are part of a pharmaceutical composition. Pharmaceutical compositions, comprising an effective amount of such a compound in a pharmaceutically acceptable carrier, can be administered to a patient, person, or animal having a disease, disorder, or condition as described herein.

The amount of compound which will be effective in the treatment of a particular disease, disorder, or condition will depend on the nature of the disease, disorder, or condition, and can be determined by standard clinical techniques. Where possible, it is desirable to determine in vitro the cytotoxicity of the compound to the tissue type to be treated, and then in a useful animal model system prior to testing and use in humans.

The compounds can be administered by any conventional means available for use in conjunction with pharmaceuticals, either as individual therapeutic agents or in a combination of therapeutic agents. Each can be administered alone, but is preferably administered with a pharmaceutical carrier selected on the basis of the chosen route of administration and standard pharmaceutical practice. The pharmaceutical compositions of the invention can be adapted for oral, and parenteral administration, and can be in unit dosage form, in a manner well known to those skilled in the pharmaceutical art. Parenteral administration includes but is not limited to, injection subcutaneously, intravenously, intraperitoneally or intramuscularly. Oral application is preferred, however.

For oral administration, gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5-15% polysorbate 80 or lecithin, suitable stabilizing agents and, if necessary, buffer substances. Antioxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

As will be understood by those in the art, the compositions and pharmaceutical compositions of the invention may be provided in the form of a kit. Kits of the invention comprise one or more specific compositions and/or pharmaceutical compositions of the invention. Optionally, the kit further contains printed instructions as a label or package insert directing the use of such reagents to modify skin pigmentation, i.e., to lighten skin as appropriate to the particular included composition. These compounds are provided in a container designed to prevent contamination, minimize evaporation or drying of the composition, etc. The compounds may or may not be provided in a preset unit dose or usage amount.

General Methods of Preparation

The compounds of this invention can be purchased from commercial sources and tested for their activities. The test compounds which are not commercially available can be prepared from readily available starting materials using various general methods and procedures known in the art. For example, the compounds may be synthetically prepared from known starting materials by conventional laboratory procedures and protocols. Likewise, those compounds that may be found in existing natural materials may be isolated and/or purified by known procedures, to attain the requisite concentration and content of the active, to be efficacious when formulated into compositions in accordance with the present invention. Such preparations may also be described as formulations or materials that are enriched for the particular compound(s) of the invention, and the present invention embraces such preparations within its scope.

Additionally, as will be apparent to those skilled in the art with respect to the methods of preparation of the compounds of the invention involving organic synthesis, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

Materials:

L-cystine (99%), cystamine dihydrochloride (98%), L-cystine dimethylester dihydrochloride (≥95%) (CDME), N-(2-Mercaptopropionyl)glycine (Thiola), $N_\alpha,N_\alpha'$-di-Boc-L-cystine (cystine-boc), N-acetyl-L-cysteine methyl ester (ALCME), N-acetyl-L-cysteine (ALC), cystamine, L-Homocystine, L-serine methyl ester (SME), poly(acrylic acid) partial sodium salt (50 wt % in $H_2O$, 5 kDa), poly-L-aspartic acid sodium salt (12.3 kDa), poly-L-glutamic acid sodium salt (13.6 kDa), poly-L-lysine hydrobromide (15 kDa), poly-L-arginine hydrochloride (14 kDa), apo-transferrin (human, >98%), chondroitin (sulfate A sodium salt from bovine trachea), human serum albumin (fatty-acid free, 99%), sodium citrate (dihydrate), S-tert-butylmercapto-L-cysteine, D-penicillamine disulfide, and 3,3'-dithiodipropionic acid (99%), L-cysteine (>97%), and L-cysteine methyl ester hydrochloride (98%) (HCME) were obtained from Sigma Aldrich and used without purification. Osteopontin, extracted and purified from bovine milk, was donated by Esben Sorenson (University of Aarhus, Denmark) and contains 7 wt % $Ca^{2+}$ ions (as determined with ion chromatography). Tamm-Horsfall protein (THP) was obtained from a human sample with no personal or family history of kidney stone disease. THP was isolated and purified using previously reported procedures, and a portion of the native protein was desialylated by treatment with the enzyme neuraminidase (resulting in a 50% reduction of carbohydrate content). Type I and type III antifreeze proteins (AFPs) purified from cold ocean teleost fish were used as received from A/F Protein, Inc. (Waltham, Mass.). All solutions were prepared using deionized water (18.2 MΩ) purified with a Direct-Q 3 Millipore purification system.

Synthesis of Intermediates

The following compounds may be used as intermediates to synthesize the compounds of the invention.
Boc Protected L-Cystine Methyl Ester (CME)
Synthetic Scheme:

Scheme S1. Synthetic routes to Boc protected L-cystine methyl ester (CME)

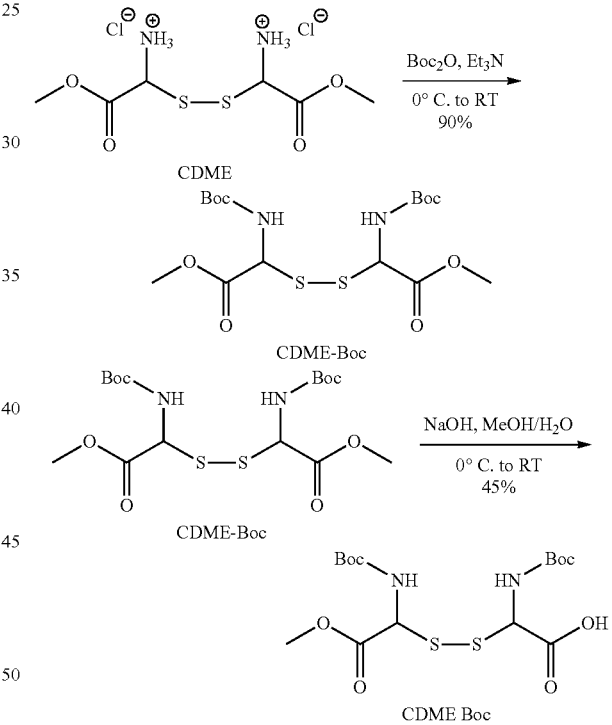

Synthesis of Cystine Dimethyl Ester Dihydrochloride (CDME)

A stream of dry hydrogen chloride gas was sparged rapidly into a suspension of cystine (10 g) in anhydrous methanol (50 mL) and agitated with a magnetic stirrer. After all the cystine had dissolved the warm solution was cooled in an ice bath, and sparging of HCl continued to saturation at 0-5° C. The reaction mixture was protected from atmospheric moisture with a calcium chloride drying tube and allowed to stand at room temperature for 3 hours. Solvent was removed from the reaction mixture under reduced pressure on a o rotary evaporator with the water bath set at 50° C. An aliquot of methanol (50 mL) was added to the resulting syrup and then concentration by rotary evaporation repeated. To the dry syrupy residue was added anhydrous ether (20 mL) resulting in spontaneous crystallization. The mixture was allowed to stand overnight at 4° C. and the resulting crystalline suspension was collected by filtration in a buchner funnel and washed with cold anhydrous ether (30 mL). The filter cake was dried under reduced pressure over potassium hydroxide pellets in a desiccator.

Synthesis of CDME-Boc $Et_3N$ (2.6 g, 17.6 mmol) was slowly added to a stirred solution of CDME (1.5 g, 4.4 mmol, Compound 2) in $CH_2Cl_2$ (20 mL) at 0° C. After stirring for 10 min, di-tert-butyl dicarbonate (T-Boc, 2.2 g, 10.12 mmol) in $CH_2Cl_2$ (20 mL) was added dropwise over the course of approximately 2 hours. The reaction was stirred overnight and allowed to slowly warm to room temperature. The mixture was extracted with $CH_2Cl_2$ (2×200 mL). The combined organic layers were dried over $Na_2SO_4$ and concentrated in vacuo. The residue was purified by column chromatography on silica gel (hexane/AcOEt=11/7) to yield the compound CDME-Boc. $^1$HNMR (400 MHz, $CDCl_3$): δ=5.4 (br, 2H), 4.6 (br, 2H), 3.8 (s, 6H) 1.45 (s, 18H). $^1$HNMR spectra of CDME-Boc exhibit a ratio of 3:1 for the H peak of Boc to methyl ester.

Reduction of CDME-Boc to CME-Boc

To a stirred solution of CDME-Boc (0.5 g, 1.1 mmol) in methanol (20 mL) was slowly added NaOH (0.054 g, 1.3 mmol) in water (20 mL) for approximately 2 hours at 0° C. After stirring the solution overnight and allowed it to reach room temperature, 0.5 M HCl was added to achieve a pH 1.0 solution. The mixture was extracted with $CH_2Cl_2$ (2×200 mL). The combined organic layers were dried over $Na_2SO_4$ and concentrated in vacuo. The residue was purified by column chromatography on silica gel (MeOH/$CH_2Cl_2$=1/10) to yield CME-Boc. $^1$HNMR (400 MHz, $CDCl_3$): δ=5.8 (br, 2H), 4.5 (br, 2H), 3.8 (s, 3H) 1.45 (s, 18H). $^1$HNMR spectra of the CME-Boc exhibit a ratio of 6:1 for the H peak of Boc to methyl ester.

Synthesis of Compounds of the Invention

Synthesis of Oligomer Compounds of the Invention

The oligomer compounds can be prepared by following the following synthetic scheme.

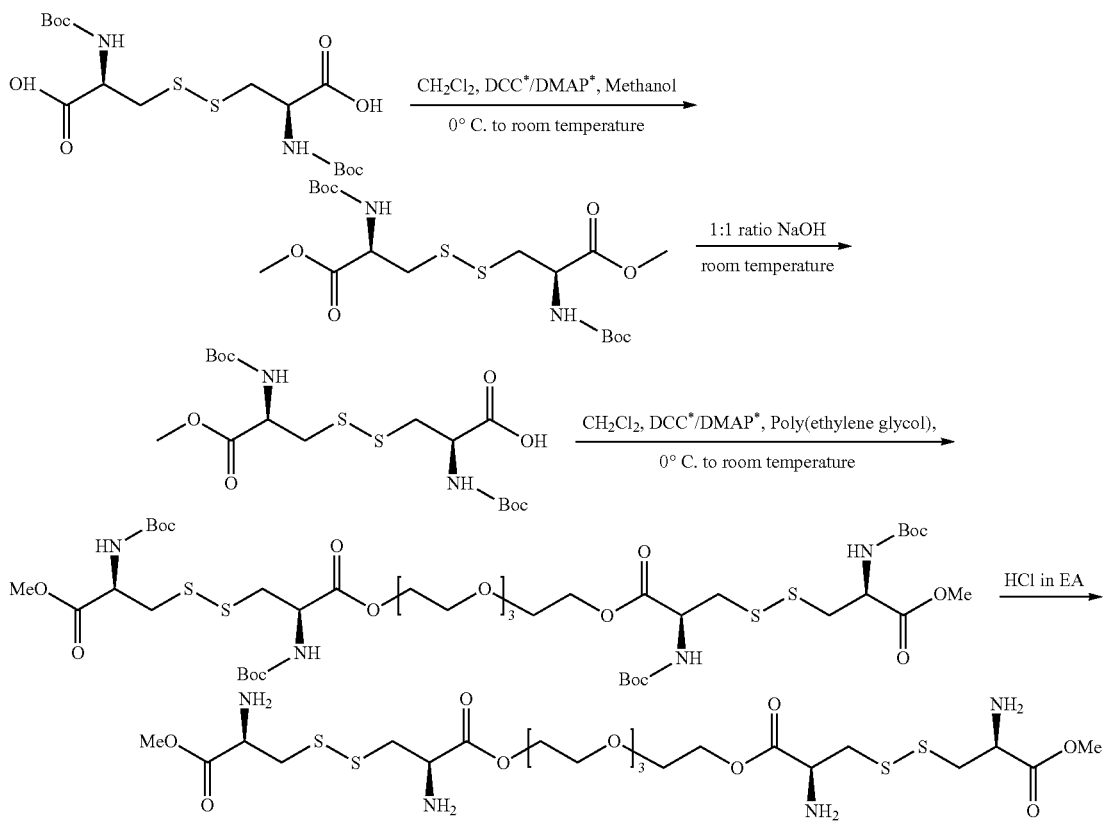

Synthesis of C—C Compounds of the Invention

The C—C analogs of cystine compounds may be prepared by following literature methods. A representative synthetic scheme which can be used to prepare the C—C compounds of the invention is given below, which is described in Synthetic Communications (2006), 36(12), 1707-1713.

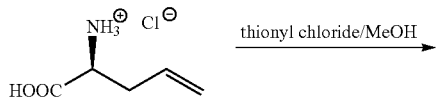

-continued

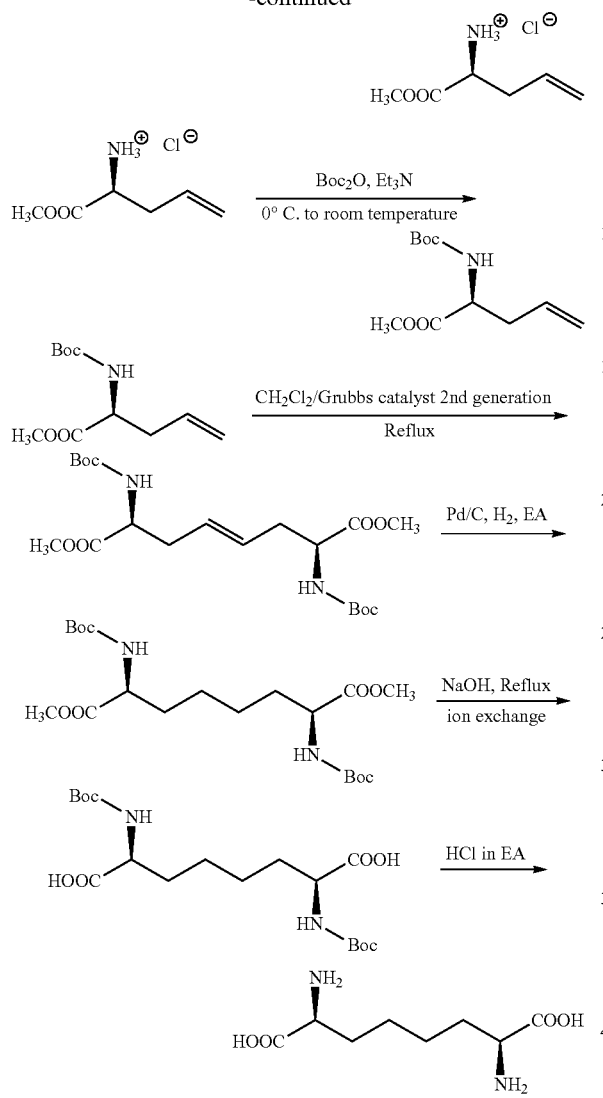

Step 1: Synthesis of L-allylglycine methyl ester(AGME)

Dissolve L-allyglycine salt (1.85 g) in 24 mL CH$_3$OH, add 2 mL thionyl chloride. The mixture was stirred overnight and allowed to slowly warm to room temperature. The residue was concentrated in vacuo. $^1$HNMR (400 MHz, CDCl$_3$): δ=5.87 (m, 1H), 5.31 (m, 2H), 4.25 (br, 1H), 3.81 (s, 1H), 2.86 (br, 2H).

Step 2: Synthesis of L-AGME-Boc

Et$_3$N (2.7 g) was slowly added to a stirred solution of L-AGME (2 g) in CH$_2$Cl$_2$ (20 mL) at 0° C. After stirring for 10 min, di-tert-butyl dicarbonate (T-Boc, 3.6 g) in CH$_2$Cl$_2$ (20 mL) was added dropwise. The reaction was stirred overnight and allowed to slowly warm to room temperature. The mixture was extracted with CH$_2$Cl$_2$ (2×200 mL). The combined organic layers were dried over MgSO$_4$ and concentrated in vacuo. $^1$HNMR (400 MHz, CDCl$_3$): δ=5.70 (m, 1H), 5.15 (m, 2H), 5.05 (br, 1H), 4.38 (m, 1H), 3.72 (s, 3H), 2.48 (m, 2H), 1.44 (s, 9H).

Step 3: Synthesis of Dimethyl (2S,7S)-Bis-(tert-butoxycarbonyl)amino-4-octenedioate (AGME-Boc dimer)

A solution of L-AGME-Boc (200 mg) in CH$_2$Cl$_2$ (6 mL) was evacuated and then bubbled with N$_2$ for 5 min, and then add the Grubbs II catalyst (58 mg) in CH$_2$Cl$_2$ (1 mL). The solution was refluxed overnight. And then the residue was concentrated in vacuo. The residue was purified by column chromatography on silica gel (Hexane/EtOAc=8/2) to yield the compound L-AGME-Boc dimer. $^1$HNMR (400 MHz, CDCl$_3$): δ=5.42 (bs, 2H), 5.13 (br, 2H), 4.35 (m, 2H), 3.75 (s, 6H), 2.47 (m, 4H), 1.45 (s, 18H).

Step 4: Synthesis of Dimethyl (2S,7S)-bis-(tert-butoxycarbonyl)aminooctanedioate (AGME-Boc-single)

Dissolve L-AGME-Boc dimer (80 mg) in ethyl acetate (20 mL), and then add 10% Pd/C (40 mg) in the solution, the solution was flushed with H$_2$ 3 times. The mixture was filled with H$_2$ and shaked over night. The mixture was purified after a short column of silica gel to get rid of Pd/C. The residue was concentrated in vacuo. $^1$HNMR (400 MHz, CDCl$_3$): δ=5.05 (br, 2H), 4.27 (br, 2H), 3.73 (s, 6H), 1.76 (m, 2H), 1.61 (m, 2H), 1.43 (s, 18H), 1.36 (m, 4H).

Step 5: Synthesis of (2S,7S)-2,7-bis((tert-butoxycarbonyl)amino)octanedioic acid (AG-Boc acid)

Dissolve L-AGME-Boc-single (0.40 g) in 10 mL CH$_3$OH, then prepare NaOH solution (0.12 g in 20 mL H$_2$O), add the NaOH solution into methanol solution, and then reflux overnight. Evaporate the methanol using vacuum evaporation, and then achieve the ion exchange using 36 (wet) ion-exchange resin during 30 mins.

Step 6: Synthesis of (1S,6S)-1,6-dicarboxyhexane-1,6-diaminium chloride(CCacid)

Add 20 mL HCl in EA (1M) into the AG-Boc acid, stir for overnight. Then evaporate to get rid of extra ethyl acetate. The mixture was extracted with CH$_2$Cl$_2$ (2×200 mL). Evaporate the H$_2$O away, get the pure solid.

$^1$HNMR (400 MHz, MeOD$_4$): δ=4.02 (tr, 1H), 1.98 (m, 2H), 1.60 (m, 2H)

Synthesis of S—C Compounds of the Invention

The S—C analogs of cystine compounds may be prepared by following literature methods. A representative synthetic scheme which can be used to prepare the S—C compounds of the invention is given below:

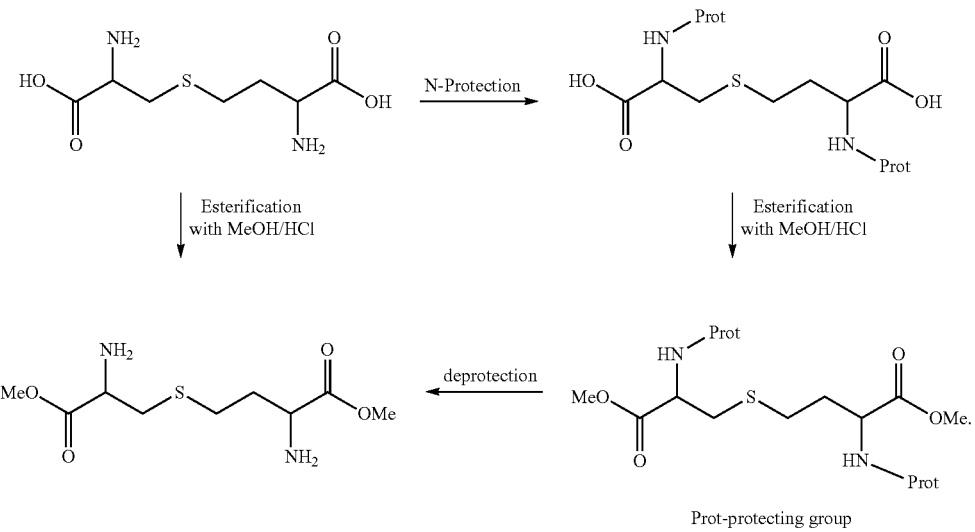

Synthesis of C=C Compounds of the Invention

The C=C analogs of cystine compounds may be prepared by following literature methods. A representative synthetic scheme which can be used to prepare the C=C compounds of the invention is given below:

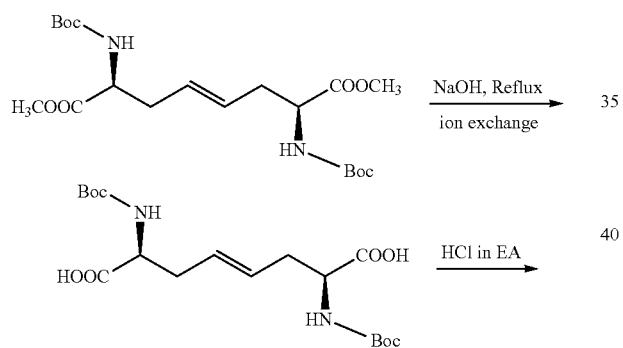

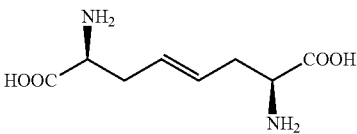

-continued

Synthesis of S—S acyl Compounds of the Invention

The S—S analogs of acyl cystine compounds may be prepared by following literature methods. A representative synthetic scheme which can be used to prepare the S—S acyl compounds of the invention is given below:

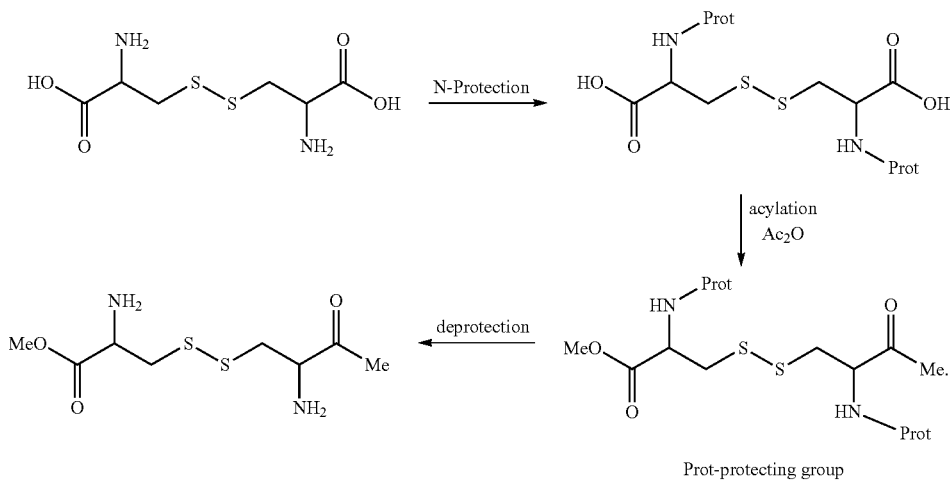

Synthetic Methods to Prepare Cystine Sulfoxides and Sulfone Derivatives

The cystine sulfoxides and sulfone derivatives may be prepared by following synthetic methods described in Tetrahedron Letters, 45(50), 9237-9240; 2004; or in Journal of Organic Chemistry, 50(22), 4332-6; 1985.

Additional General methods for sulfoxides and sulfones may be found in Tetrahedron Letters (2004), 45(50), 9237-9240.

General Synthetic Methods to Prepare N-Alkyl Cystine s Derivatives

The N-alkyl derivatives may be prepared by following synthetic methods described in Indian Journal of Chemistry, Section B: Organic Chemistry Including Medicinal Chemistry, 37B(1), 10-14; 1998; Heterocycles, 67(2), 519-522; 2006; or in Indian Journal of Chemistry, Section B: Organic Chemistry Including Medicinal Chemistry, 37B(1), 10-14; 1998

Additional methods to prepared compounds of the invention may be found in: Facile synthesis of β-amino disulfides, cystines, and their direct incorporation into peptides. Nasir, Baig R. B.; Kanimozhi, Catherine K.; Sudhir, V. Sai; Chandrasekaran, Srinivasan. Department of Organic Chemistry, Indian Institute of Science, Bangalore, India. Synlett (2009), (8), 1227-1232; and Conversion of thiosulfinate derivatives of cystine to unsymmetrical cystines and lanthionines by reaction with tris(dialkylamino)phosphines. Olsen, Richard K.; Kini, Ganesh D.; Hennen, William J. Dep. Chem. Biochem., Utah State Univ., Logan, Utah, USA. Journal of Organic Chemistry (1985), 50(22), 4332-6. CODEN: JOCEAH ISSN: 0022-3263. Journal written in English.

The synthesis of representative compounds of the invention is given below.

Example 1

Synthesis of L-Cystine Diethyl Ester Dihydrochloride

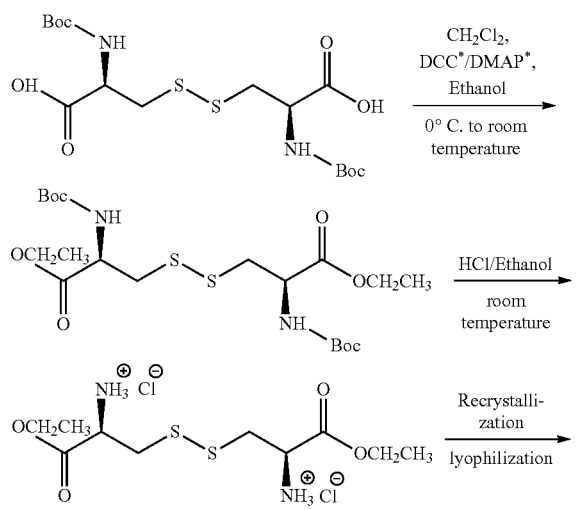

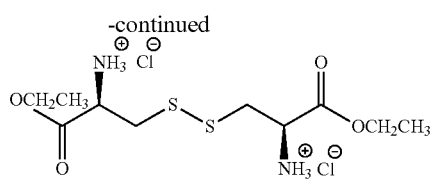

Step 1: Synthesis of L-CDEE-Boc

CH$_2$Cl$_2$ (20 mL) and ethanol (1.5 mL) were added to the L-cys-Boc (2.0 g) and DMAP (0.1 g), after stirring for 10 min, DCC(2.8 g) was added into the solution during 30 min. The reaction was stirred overnight and allowed to slowly warm to room temperature. The solution was filtered and the filtrate was concentrated in vacuo. The residue was purified by column chromatography on silica gel (hexane/EtOAc=7/3) to yield the compound L-CDEE-Boc. $^1$HNMR (400 MHz, CDCl$_3$): δ=5.39 (br, 1H), 4.46 (br, 1H), 4.05 (br, 2H), 1.45 (s, 9H), 1.20 (br, 3H). $^1$HNMR spectra were recorded using a Bruker AVANCE 400 spectrometer using broadband decoupling.

Step 2: Removal of Boc from L-CDEE-Boc 70 ml 1.25M HCl/Ethanol was added to L-CDEE-Boc (1.5 g) and the mixture was stirred overnight. The mixture was then extracted with H$_2$O (2×200 mL), L-CDEE was obtained as the hydrochloride salt after lyophilization. The salt was crystallized from ethanol/ethyl acetate to give the pure L-CDEE. $^1$HNMR (400 MHz, D$_2$O): δ=4.38 (br, 2H), 4.23 (br, 2H), 3.33 (br, 2H), 1.272 (s, 6H).

Example 2

Synthesis of L-cystine isopropyl ester (L-CDIE)

The compound was prepared following the procedure used to prepare CDEE. For CDIE preparation ethanol was replaced with isopropanol.

L-CDIE-Boc: $^1$HNMR (400 MHz, CDCl$_3$): δ=5.42 (br, 1H), 5.07 (br, 1H), 4.56 (br, 1H), 3.17 (br, 2H), 1.45 (s, 9H), 1.16 (br, 6H). L-CDIE salt: $^1$HNMR (400 MHz, D$_2$O): δ=5.08 (br, 1H), 4.45 (br, 1H), 3.30 (br, 2H), 1.250 (s, 6H).

Example 3

Synthesis of L-cystine di-tert-butyl ester (L-CDTE)

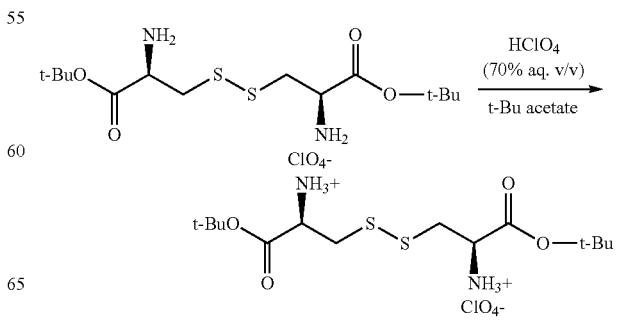

Synthesis of L-cystine di-tert-butyl ester perchlorate(CDTE)

L-Cystine (10.0 g, 42 mmol) is dissolved in perchloric acid (70% aq. v/v, 16.6 mL) and treated slowly with 100 mL tert-butyl acetate. After stirring the mixture for overnight, a white solid is separated. The mixture is cooled on ice for 30 min and the solid is collected by filtration, washed with cold ethyl ether and dried to yield the pure solid of L-CDTE perchlorate.

L-CDTE perchlorate: $^1$HNMR (400 MHz, $CD_3OD$): δ=4.35 (br, 1H), 3.40 (m, 1H), 3.25 (m, 2H), 1.56 (s, 9H).

Example 4

Synthesis of L-Homocystine Dimethyl Ester Dihydrochloride(HOMOME)

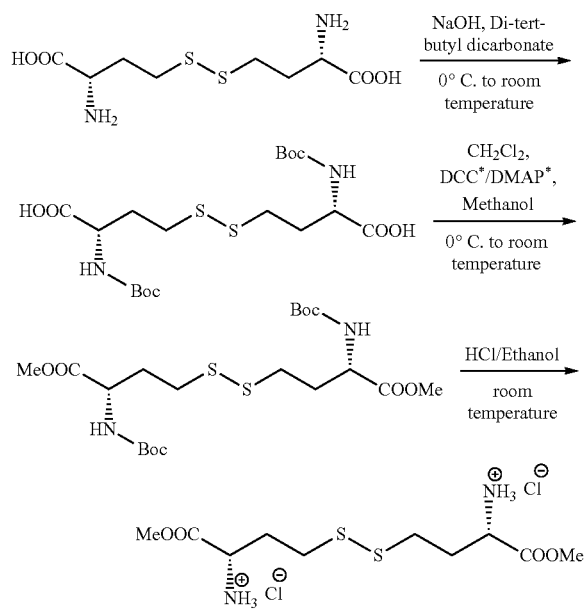

Step 1: Synthesis of L-homocystine-Boc

L-homocystine (0.50 g) was dissolved in 20 mL 1,4-dioxane and treated with NaOH solution (0.313 g in 20 mL $H_2O$). The mixture was stirred for 10 min. and then treated with di-tert-butyl carbonate (1.02 g). The reaction was stirred overnight and was allowed to warm to room temperature slowly. 10 mL HCl (1M) was then added into the mixture to adjust pH to 1, and the mixture was extracted using ethyl acetate. The organic layer was separated and the solvent was removed to give the crude homocystine-boc, as a white solid.

Step 2: Synthesis of L-homocystine dimethyl ester-Boc (L-homome-boc)

$CH_2Cl_2$ (20 mL) and methanol (2 mL) were added to the L-homocystine-Boc (0.80 g) and DMAP (0.1 g). After stirring for 10 min, DCC (1.05 g) was added into the solution over a period of 30 min. The reaction was stirred overnight and allowed to warm to room temperature slowly. The solution was filtered and the filtrate was concentrated in vacuo. The residue was purified by column chromatography on silica gel (hexane/EtOAc=7/3) to yield the compound L-homome-Boc. $^1$HNMR (400 MHz, $CDCl_3$): δ=5.10 (br, 1H), 4.42 (br, 1H), 3.72 (s, 3H), 2.72 (br, 2H), 2.25 (br, 1H), 2.05 (br, 1H), 1.45 (s, 9H).

Step 3: Removal of Boc from L-homome-Boc 20 ml 1.25M HCl/ethyl acetate was added to L-homome-Boc (0.5 g) and the mixture was stirred overnight. The mixture was then extracted with $H_2O$ (2×200 mL). Homome was obtained as the hydrochloride salt after lyophilization. $^1$HNMR (400 MHz, $CD_3OD$): δ=4.24 (br, 2H), 4.10 (br, 2H), 3.91 (s, 3H), 2.81 (br, 2H), 2.48 (br, 2H).

Crystallization of L-Cystine

Preparation of Hexagonal L-Cystine Crystals

Syntheses of L-cystine reported in the literature vary in approach, often employing acidic solutions (pH<1) that generate three crystalline structures: L-cystine dihydrochloride, L-cystine dihydrochloride dihydrate, and L-cystine (hexagonal). A reported protocol for recrystallization of L-cystine in 0.5% HCl was followed [S1], which yielded largest crystals with (0001) surfaces void of observable steps, as confirmed by AFM topographical imaging that revealed roughened surfaces without terraces. This protocol was modified by using solutions at physiological pH (i.e. pH~7), which generated hexagonal crystals with multiple, terraced steps that were visible even by optical microscopy. Hexagonal L-cystine crystal platelets were synthesized for AFM measurements of surface topography and real time in situ growth. A supersaturated L-cystine solution was prepared by adding 70 mg of L-cystine to a 250 mL round-bottom flask containing 100 mL of deionized water. A heating mantle was pre-heated for 10 min, and then the supersaturated L-cystine solution was refluxed at 100° C. for 20 min with stirring to completely dissolve L-cystine. The boiling solution was gradually cooled on the heating mantel while continuously condensing and stirring for 75 min. The solution was then transferred into a 100 mL beaker, sealed to prevent evaporation and exposure to airborne particulates, and stored overnight at room temperature without stirring. Single crystals were collected by vacuum filtration (Whatman Grade 1 filters, >11 μm pores) and were air dried prior to analysis.

Alternatively, the hexagonal crystals can be obtained by crystallization performed near neutral pH (Sa) The hexagonal form was crystallized from a supersaturated L-cystine solution prepared by adding 70 mg of L-cystine to 100 mL of deionized water (3 mM), and heating under reflux at 100° C. for 20 min with stirring to completely dissolve L-cystine. The resulting solution corresponds to a relative supersaturation of σ~7.5, based on the lower bound of reported solubility (0.4-0.7 mM at pH 7, 25° C.) (Sb, Sc, Sd). This concentration was used for bulk crystallization studies in the presence of additives so that a measurable amount of bulk crystals could be obtained in a reasonable time. The solution was then allowed to cool slowly with stirring for 75 min. 30 mL aliquots were transferred to separate glass containers, which were then sealed to prevent evaporation and exposure to airborne particulates and stored for 72 hours at room temperature without stirring. Single crystals were collected by vacuum filtration (Whatman Grade 1 filters, >11 μm pores) and were air dried prior to analysis. The crystals retrieved in this manner were used for AFM studies by mounting individual crystals according to the procedure described below.

Bulk Crystallization in the Presence of Compounds of the Invention (Additive).

The compounds of the present invention may be prepared and tested for their crystal growth inhibition properties using the procedures described herein. For example, the aforementioned procedure for hexagonal platelet crystallization is repeated. Following the 75 min cooling period, prior to any observable crystallization, a compound of the invention is added to the supersaturated L-cystine solution to the desired concentration. The container is sealed and stored for 72 hours at room temperature without stirring, after which the precipitate is collected by vacuum filtration (Whatman Grade 1 filters, >11 μm pores) and is air dried prior to analysis. Crystallization without additive is performed in an identical manner for comparison using a control solution from the same batch. The mass yields of L-cystine crystals are obtained by dividing the mass of L-cystine crystals (collected from growth solution by filtration) by the mass of L-cystine added in the growth solution. The crystals are isolated with 11 μm-pore filters, which are regarded as sufficiently small for reliable capture of the crystals (optical micrographs reveal that the size of crystals is always greater than 50 μm.

Materials Characterization

An Orion 3 Star pH meter (Thermo Electron Corp.) with Orion 9157BNMD probe is used to measure the pH of L-cystine solutions. Crystal morphology is measured with a Leitz ERGOLUZ optical microscope and a Hitachi 3500 scanning electron microscopy. A thin coating of gold (2 nm) is sputtered on SEM samples and images are acquired at low voltage (2-5 kV) to minimize sample melting. $^1$H NMR spectra are recorded using a Bruker AVANCE 400 spectrometer and are routinely run using broadband decoupling. Chemical shifts (δ), expressed in ppm, are referenced to the corresponding residual nuclei in deuterated solvent ($D_2O$). Powder X-ray diffraction (XRD) patterns of isolated crystals are acquired with a Panalytical XPert PRO MPD using a Bragg-Brentano geometry with fixed slits at power settings of 45 kV and 40 mA. A CuKα radiation (0.154 nm) source is used with a 1 degree fixed divergence slit (10 mm beam mask) for incident X-rays and a 1 degree anti-scatter slit Ni filter (1/16 degree peceiving slit) for diffracted X-rays.

Single Crystal X-Ray Diffraction (SCXRD):

Patterns are acquired with a Bruker SMART ApexII CCD area detector on a D8 goniometer. The temperature during the data collection is controlled with an Oxford Cryosystems Series 700 plus instrument. Preliminary lattice parameters and orientation matrices are obtained from three sets of frames. Data are collected using graphite-monochromated and 0.5 mm-MonoCap-collimated Mo—$K_α$ radiation (λ=0.71073 Å) with the ω scan method (Bruker APEXII). Data are processed with the SAINT+ program for reduction and cell refinement. Multi-scan absorption corrections are applied by using the SADABS program for area detector. The structure is solved by the direct method (SHELXS-97) and refined on $F^2$ (SHELXL-97) (G. M. Sheldrick, Universität Göttingen, Germany).

AFM Characterization:

A Digital Instruments (Santa Barbara, Calif.) Nanoscope Ma Multimode system is used for topographical and lattice imaging. All measurements are performed in contact mode using Veeco NP—B $Si_3N_4$ cantilever tips with a spring constant of 0.12N/m (triangular, 196 μm length, 41 μm width) on a glass cantilever holder, and a liquid cell is created for in situ step velocity measurements. All L-cystine crystals for AFM measurements are prepared by the method described herein. Crystals are transferred onto an AFM specimen disk coated with partially cured (1 hr) UV-curable optical cement (Type SK-9, EMS Acquisition Corp.) by gently pressing the disk against hexagonal platelets or L-cystine needles isolated by filtration (Whatman Nuclepore membrane, 8 μm). The (0001) face of hexagonal platelets is exposed normal to the disk for AFM analysis with growth occurring along equivalent {1010} faces in the lateral directions, while the sides of L-cystine needles are exposed normal to the disc. The partially cured polymer with adhered crystals is completely cured by additional UV radiation (2 hrs) prior to analysis. Measurements of individual step heights for hexagonal L-cystine crystals are acquired in air (contact mode) at a scan rate of 1.00 Hz and 256 samples per line over a 15×15 μm$^2$ surface area. Integral and proportional gains are set to the highest possible values without obtaining feedback. Four hexagonal crystals (5 areas per crystal) are analyzed for statistical step height distributions, which are calculated from >10$^3$ individual steps. Lattice-resolved images of crystal surfaces are acquired in water (contact mode) using a scan rate of 112 Hz over a 12×12 nm$^2$ area.

In Situ AFM Growth Measurements:

Real time in situ step velocity measurements of L-cystine growth are assessed along six structurally-equivalent {1010} faces of the hexagonal structure. A liquid cell is created with the glass cantilever tip holder, and working solutions are injected through a 1-mL syringe. Prior to injecting the growth medium (i.e. supersaturated L-cystine solution), crystals are etched with deionized water in the fluid cell for one hour to remove amorphous deposits or impurities that may be present on the surface. Supersaturated solutions (0.5 g/L) are generated by adding L-cystine to deionized water, boiling the solution on a heating mantle for 20 min to completely dissolve the solute, and allowing the solution to cool for 20 min on the heating mantle before transferring the solution (via syringe) to the AFM fluid cell. This method allows the solution to gradually cool to room temperature prior to AFM measurements in an effort to minimize premature nucleation of L-cystine in the growth solution.

The effect of the compound of invention (additives) on crystal growth rates is investigated. Additives are combined with the supersaturated L-cystine following the 20 min cool down period (as discussed above) to avoid denaturing biological additives at higher temperature. A small volume (0.2 mL) of concentrated additive is mixed with 4.8 mL of L-cystine to generate 0.48 g/L L-cystine solutions with additives of varying concentrations. Control measurements without additive are performed in a similar manner, replacing concentrated additive solutions deionized water to maintain a constant L-cystine concentration. Data collection is started immediately after injecting the working solution into the AFM liquid cell. For each measurement, growth is first assessed in the absence of additive, then in the presence of additive on the identical area of the crystal surface to analyze relative changes in step velocity. Measurements are acquired at static conditions without refreshment of growth solution using supersaturated L-cystine solutions six times larger than the solubility of L-cystine in water, which is reported as 0.4-0.7 mM (pH 7, 25° C.). At these conditions, step advancement is observable at a reasonable timescale; however, supersaturated solutions with L-cystine concentrations three times solubility did not result in step growth during the time of measurement. At static conditions, solute is depleted from solution during growth, leading to a slight decrease in the step velocity with increasing time. As such, the total number of crystals adhered to the sample disk are minimized to lower the total surface area of crystals exposed to the growth solution, thereby minimizing depletion of solute. Topographical images are acquired at maximal integral and proportional gains (i.e. without feedback) using a scan rate of 5.1 Hz (256 samples per line) and a scan area of 5×5 μm². Crystal growth on the (0001) surface is measured as the distance a step advanced with time using consecutive deflection images where the acquisition time for each complete scan is approximately 50 sec.

The AFM measurement data obtained for the compounds of invention is tabulated in Table 1, below, wherein $V_o$ is the velocity of step advancement in the absence of prospective inhibitors; V is the velocity of step advancement in the presence of a prospective inhibitor; $V/V_o$ is the normalized velocity, that is, the ratio of the velocity in the presence of the inhibitor to the velocity in the absence of inhibitor (lower values are tantamount to more effective inhibition); $V_o/V$ is the inverse of $V/V_o$ (higher values are tantamount to more effective inhibition).

TABLE 1

Inhibitory Data for Compounds of Invention

| # | Name | Full Name | Structure | Concentration (nM) | V/Vo | Vo/V |
|---|------|-----------|-----------|--------------------|------|------|
| 1 | CDME | L-cystine dimethyl ester | 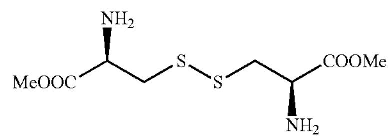 [SMILES: COC(=O)[C@@H](N)CSSC[C@H](N)C(=O)OC] | 0.015 | 0.38 | 2.62 |
| 2 | CDPE | L-cystine diphenyl ester | 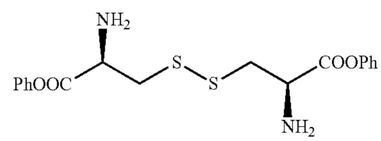 | 0.015 | 0.41 | 2.44 |
| 3 | HCME | L-cysteine methyl ester | 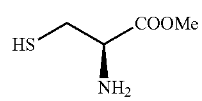 | 0.03 | 0.49 | 2.05 |
| 4 | CDEE | L-cystine diethyl ester | 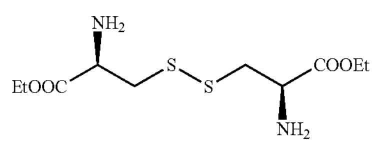 [SMILES: CCOC(=O)[C@@H](N)CSSC[C@H](N)C(=O)OCC] | 0.015 | 0.56 | 1.79 |
| 5 | HOMOME | L-homocystine dimethyl ester | 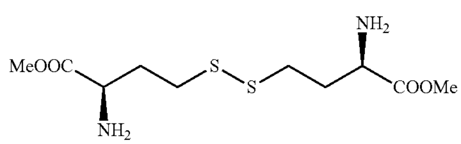 [SMILES: COC(=O)[C@H](N)CCSSCC[C@@H](N)C(=O)OC] | 0.015 | 0.63 | 1.59 |
| 6 | CDIE | L-cystine diisopropyl ester | 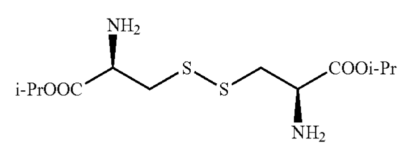 | 0.015 | 0.64 | 1.55 |
| 7 | CME | L-cystine methyl ester | 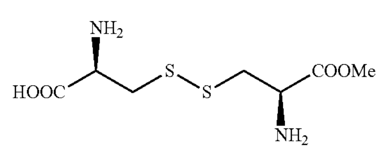 [SMILES: COC(=O)[C@@H](N)CSSC[C@H](N)C(=O)O] | 0.015 | 0.68 | 1.47 |
| 8 | CDTE | L-cystine ditert-butyl ester | 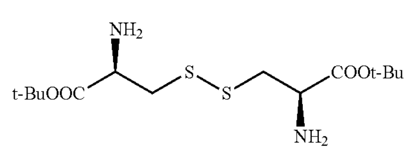 | 0.015 | 0.7 | 1.43 |
| 9 | thiola | N-(2-Mercaptopropionyl) glycine | 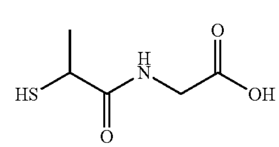 | 0.03 | 0.74 | 1.35 |

TABLE 1-continued

Inhibitory Data for Compounds of Invention

| # | Name | Full Name | Structure | Concentration (nM) | V/Vo | Vo/V |
|---|---|---|---|---|---|---|
| 10 | C=CME | L-dimethyl 2,7-diamino oct-4-enedioate | 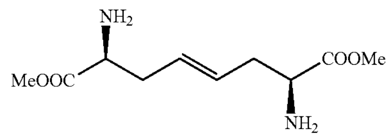 [SMILES: COC(=O)[C@@H](N)C/C=C/C[C@H](N)C(=O)OC] | 0.015 | 0.81 | 1.23 |
| 11 | Cystine-Boc | $N_\alpha,N_\alpha'$-di-Boc-L-cystine | 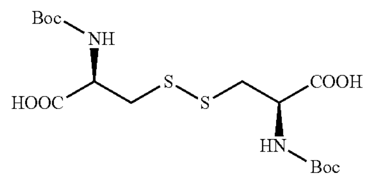 [SMILES: CC(C)(C)OC(=O)N[C@@H](CSSC[C@H](NC(=O)OC(C)(C)C)C(=O)O)C(=O)O] | 0.09 | 0.81 | 1.23 |
| 12 | CCME | L-dimethyl 2,7-diamino octanedioate | 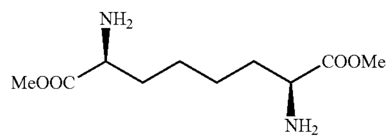 [SMILES: COC(=O)[C@@H](N)CCCC[C@H](N)C(=O)OC] | 0.015 | 0.92 | 1.09 |
| 13 | ALCME | N-acetyl-L-cysteine methyl ester | 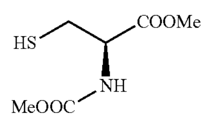 [SMILES: COC(=O)N[C@@H](CS)C(=O)OC] | 0.03 | 0.96 | 1.05 |
| 14 | Ccacid | L-diaminooctanedioic acid | 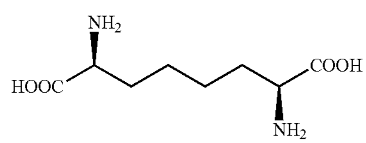 [SMILES: N[C@@H](CCCC[C@H](N)C(=O)O)C(=O)O] | 0.015 | 0.97 | 1.03 |
| 15 | ALC | N-acetyl-L-cysteine | 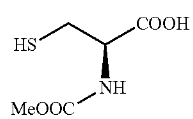 [SMILES: COC(=O)N[C@@H](CS)C(=O)O] | 0.03 | 0.99 | 1.02 |
| 16 | Cystamine | cystamine | 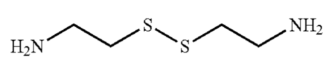 | 0.015 | 1 | 1 |
| 17 | cysteine | L-cysteine | 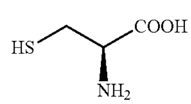 | 0.03 | 1 | 1 |
| 18 | Homocystine | L-Homocystine | 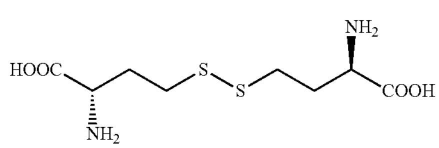 [SMILES: N[C@H](CCSSCC[C@H](N)C(=O)O)C(=O)O] | 0.015 | 1.05 | 0.95 |
| 19 | SME | L-serine methyl ester | 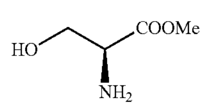 | 0.03 | 1.07 | 0.93 |

X-Ray Diffraction

There are four reported crystal structures of L-cystine having hexagonal, tetragonal, and monoclinic structures. Single crystal X-ray diffraction (SCXRD) measurements of L-cystine crystals yielded unit cell parameters that agree with reported structural data (Table 2). The small size of L-cystine tetragonal needles required a synchrotron X-ray source to obtain the unit cell parameters.

TABLE 2

Comparison of crystal unit cell parameters

| Compound | Ref | Space Group | Unit Cell Parameters (A) | | | Cell Angles (deg) | | | Volume ($A^3$) |
|---|---|---|---|---|---|---|---|---|---|
| | | | a | b | c | α | β | γ | |
| $C_6H_{14}N_2O_4S_2^{2+}$ 2(Cl$^-$) | [S5] | C2 | 18.6 | 5.3 | 7.2 | 90 | 103.6 | 90 | 687 |
| | OW | | 18.5 | 5.2 | 7.3 | 90 | 104.1 | 90 | 678 |
| $C_6H_{14}N_2O_4S_2^{2+}$2(Cl$^-$) 2($H_2O$) | [S6] | $P2_1$ | 5.9 | 13.2 | 9.4 | 90 | 90.8 | 90 | 728 |
| | OW | | 5.9 | 13.2 | 9.3 | 90 | 90.6 | 90 | 717 |
| $C_6H_{12}N_2O_4S_2$ (Hexagonal) | [S7] | $P6_122$ | 5.4 | 5.4 | 56.2 | 90 | 90 | 120 | 1433 |
| | OW | | 5.4 | 5.4 | 57.0 | 90 | 90 | 120 | 1455 |
| $C_6H_{12}N_2O_4S_2$ | [S8] | $P4_1$ | 6.7 | 6.7 | 21.7 | 90 | 90 | 90 | 978 |
| | OW | | 6.7 | 6.7 | 21.6 | 90 | 90 | 90 | 971 |
| $C_8H_{14}N_2O_4S_2^{2+}$ 2(Cl$^-$) $H_2O$ | [S9] | $P2_1$ | 5.9 | 9.3 | 14.8 | 90 | 91.5 | 90 | 808 |
| | OW | | 5.9 | 9.1 | 14.9 | 90 | 91.6 | 90 | 831 |

[5] Steinrauf et al.,
[6] Kominami et al.,
[7] Oughton et al.,
[8] Chaney et al.,
[9] Vijayalakshmi et al.;
OW = Our work While certain of the preferred embodiments of the present invention have been described and specifically exemplified above, it is not intended that the invention be limited to such embodiments. Various modifications may be made thereto without departing from the scope and spirit of the present invention, as set forth in the following claims.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds given in this application were generated using various commercially available chemical naming software tools including MDL's ISIS Draw Autonom Software tool, and were not verified. Particularly, in the event of inconsistency, the depicted structure governs.

REFERENCES

1. Dolin, D. J., et al. *J. Endourology*, 2005. 19(3): 429-432.
2. Mattoo, A. and Goldfarb, D. S. *Seminars in Nephrology*, 2008. 28(2): 181-191.
3. Moe, O. W. *Lancet*, 2006. 367(9507): 333-344.
4. Becker, G. *Nephrology*, 2007. 12: S4-S10.
5. Nakagawa, Y., et al. *J. Urol.*, 2000. 164(5): 1481-1485.
6. Moggach, S. A., et al. *J. Synchrotron Radiation*, 2005. 12: 598-607.
7. Dahaoui, S., Pichon-Pesme, V., Howard, J. A. K., and Lecomte, C. *J. Phys. Chem. A*, 1999. 103(31): 6240-6250.
8. Girija, E. K., Kalkura, S. N., and Ramasamy, P. *J. Mater. Sci. Mater. Med.*, 1995. 6(11): 617-619.
9. Fujiki, Y., Tokunaga, N., Shinkai, S., and Sada, K. *Angew. Chem. Int. Ed.*, 2006. 45(29): 4764-4767.
10. Chaney, M. O. and Steinrau. Lk. *Acta Cryst. B*, 1974. B 30 (March 15): 711-716.
11. Steinrauf, L. K., Peterson, J., and Jensen, L. H. *J. Amer. Chem. Soc.*, 1958. 80(15): 3835-3838.
12. Kominami, S., Riesz, P., Akiyama, T., and Silverton, J. V. *J. Phys. Chem.*, 1976. 80(2): 203-210.
13. Carta, R. and Tola, G. *J. Chem. Eng. Data*, 1996. 41(3): 414-417.
14. Kuzmenko, I., et al. *Science*, 1996. 274(5295): 2046-2049.
15. Weinbach, S. P., et al. *Science*, 1994. 264(5165): 1566-1570.
16. Weissbuch, I., Addadi, L., Lahav, M., and Leiserowitz, L. *Science*, 1991. 253(5020): 637-645.
17. Graether, S. P., et al. *Nature*, 2000. 406(6793): 325-328.
18. Graham, L. A. and Davies, P. L. Science, 2005. 310 (5747): 461-461.
19. Liou, Y. C., Tocilj, A., Davies, P. L., and Jia, Z. C. *Nature*, 2000. 406(6793): 322-324.
20. Sonnichsen, F. D., Sykes, B. D., Chao, H., and Davies, P. L. *Science*, 1993. 259(5098): 1154-1157.
21. Orme, C. A., et al. *Nature*, 2001. 411(6839): 775-779.
22. Stephenson, A. E., et al. *Science*, 2008. 322(5902): 724-727.
23. Sheng, X. X., Jung, T. S., Wesson, J. A., and Ward, M. D. *Proc. Nat. Acad. Sci. U.S.A.*, 2005. 102(2): 267-272.
24. DeYoreo, J. J. and Dove, P. M. *Science*, 2004. 306(5700): 1301-1302.
25. Grohe, B., et al. *J. Am. Chem. Soc.*, 2007. 129(48): 14946-14951.
26. Sizemore, J. P. and Doherty, M. F. Cryst. Growth Des., 2009. 9(6): 2637-2645.
27. Jung, T., et al. Langmuir, 2004. 20(20): 8587-8596.
28. Kessler, A., et al. *Neurochem. Res.*, 2008. 33(5): 737-744.
29. Wilmer, M. J., et al. *Pediatric Res.*, 2007. 62(2): 151-155.
30. Foreman, J. W., et al. *Metabolism Clin. & Experimental*, 1987. 36(12): 1185-1191.
S1. Fujiki, Y., Tokunaga, N., Shinkai, S., and Sada, K. *Angew. Chem. Int. Ed.*, 2006. 45(29): 4764-4767.
S2. Carta, R. and Tola, G. *J. Chem. Eng. Data*, 1996. 41(3): 414-417.
S3. Kallistratos, G. and Malorny, G. *Arzneimittel-Forschung*, 1972. 22(9): 1434-&.
S4. Konigsberger, E., Wang, Z. H., and Konigsberger, L. C. *Monatshefte Fur Chemie*, 2000. 131(1): 39-45.

S5. Steinrauf, L. K., Peterson, J., and Jensen, L. H. *J. Amer. Chem. Soc.*, 1958. 80(15): 3835-3838.
S6. Kominami, S., Riesz, P., Akiyama, T., and Silverton, J. V. *J. Phys. Chem.*, 1976. 80(2): 203-210.
S7. Oughton, B. M. and Harrison, P. M. *Acta Crystallographica*, 1959. 12(5): 396-404.
S8. Chaney, M. O. and Steinrau. Lk. *Acta Cryst. B*, 1974. B 30 (March 15): 711-716.
S9. Vijayalakshmi, B. K. and Srinivasan, R. *Acta Cryst. B*, 1975. B 31 (April 15): 993-998.
S10. Eldjarn, L. and Hambraeus, L. *Scand. J. Clin. Lab. Invest.*, 1964. 16(2): 153-&.
S11. Theriault, Y. and Rabenstein, D. L. *Canadian J. Chem.*, 1985. 63(8): 2225-2231.

What is claimed is:

1. A method for preventing, inhibiting or slowing the growth of L-cystine crystallization in a subject where such growth is present comprising administering to the subject an effective amount of a compound of formula I:

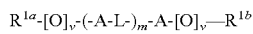

or a pharmaceutically acceptable salt, solvate, cocrystal, or prodrug thereof, and stereoisomers, tautomers and isotopic variants thereof; and wherein
each A is independently

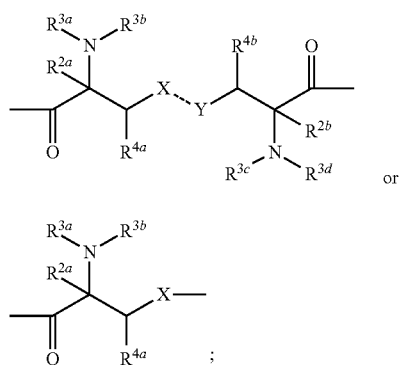

each X and Y is independently S, S(O), S(O)$_2$, or C(R$^5$)$_q$;
each R$^{2a}$, R$^{2b}$, R$^{3a}$, R$^{3b}$, R$^{3c}$, R$^{3d}$, R$^{4a}$, and R$^5$ is independently selected from H, substituted or unsubstituted alkyl, substituted or unsubstituted aryl, substituted or unsubstituted aralkyl, and substituted or unsubstituted cycloalkyl; the subscript q is 1 or 2;
the dotted bond is a single or a double bond;
provided that when one of X and Y is S, S(O), or S(O)$_2$, then the dotted bond is a single bond;
  L is —O—C$_1$-C$_6$ alkylene-O—, —O-aryl-O—, or a group —O—(CH$_2$—CH$_2$—O—)$_t$; the subscript t is 1-10; the subscript m is 0-10; and
  each R$^{1a}$ and R$^{1b}$ is independently selected from H, substituted or unsubstituted alkyl, substituted or unsubstituted aryl, substituted or unsubstituted aralkyl, and substituted or unsubstituted cycloalkyl; and each subscript v is 0 or 1; and
  when A is Ia', both X and Y are S, S(O), or S(O)$_2$, and m is 0, then each subscript v is 0; and when A is Ib', X is S, and m is 0, then each subscript v is 0.

2. A method according to claim 1 wherein the compound is of formula I; the subscript m is 0; the subscript v is 0; and the compound is according to formula II:

and wherein A, R$^{1a}$ and R$^{1b}$ are as in claim 1.

3. A method according to claim 1, wherein the compound is of formula IIIa, IIIb, IIIc, IIId, IIIe, or IIIf:

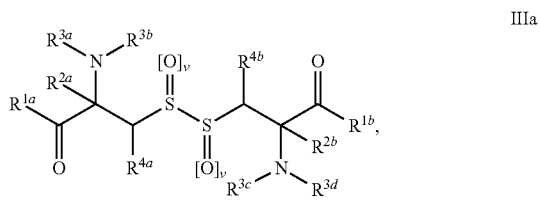

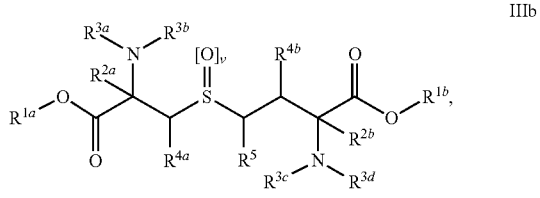

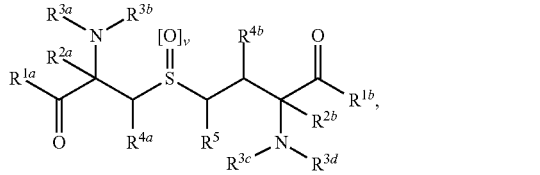

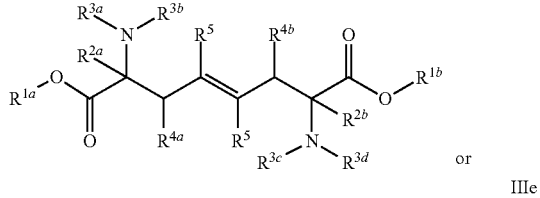

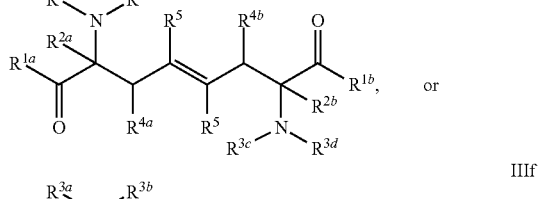

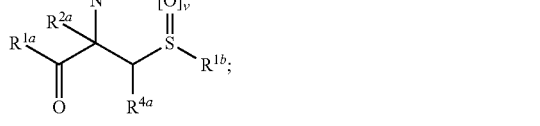

or a pharmaceutically acceptable salt, solvate, cocrystal, or prodrug thereof, and stereoisomers, tautomers and isotopic variants thereof; and wherein
  each R$^{1a}$ and R$^{1b}$ is independently selected from H, substituted or unsubstituted alkyl, substituted or unsubstituted alkenyl, substituted or unsubstituted alkynyl, substituted or unsubstituted aryl, substituted or unsubstituted aralkyl, and substituted or unsubstituted cycloalkyl;
  each R$^{2a}$, R$^{2b}$, R$^{3a}$, R$^{3b}$, R$^{3c}$, R$^{3d}$, R$^{4a}$, and R$^5$ is independently selected from H, substituted or unsubstituted alkyl, substituted or unsubstituted aryl, substituted or unsubstituted aralkyl, and substituted or unsubstituted cycloalkyl; and the subscript v of formula IIIa, IIIb, IIIc, or IIIf is 0, 1, or 2.

4. The method of claim 1, wherein the compound is according to formula IVa, IVb, IVc, IVd, IVe, IVf, Va, Vb, Vc, Vd, Ve, Vf, Vg, Vh, VIa, VIb, VIc, VId, VIIa, VIIb, VIIc, VIId, XIIa, XIIb, XIIc, or XIId:

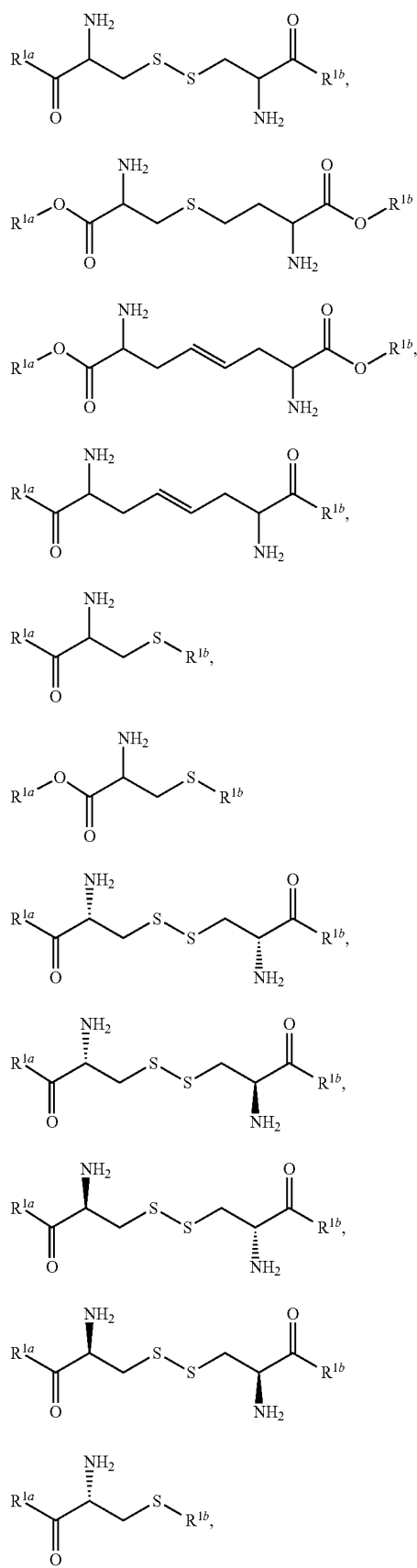

and wherein $R^{1a}$ and $R^{1b}$ are as in claim 1;

or a pharmaceutically acceptable salt, solvate, cocrystal, or prodrug thereof, and stereoisomers, tautomers and isotopic variants thereof.

5. The method of claim 1, wherein one of $R^{1a}$ and $R^{1b}$ is H; and the other is alkyl or aryl.

6. The method of claim 1, wherein one of $R^{1a}$ and $R^{1b}$ is H; and the other is Me, Et, n-Pr, i-Pr, n-Bu, t-Bu, or Ph.

7. The method of claim 1, wherein each of $R^{1a}$ and $R^{1b}$ is alkyl, cycloalkyl, or aryl.

8. The method of claim 1, wherein each of $R^{1a}$ and $R^{1b}$ is independently Me, Et, n-Pr, i-Pr, n-Bu, t-Bu, cyclohexyl, cyclopropyl, or Ph.

9. The method of claim 1, wherein each of $R^{1a}$ and $R^{1b}$ is alkenyl.

10. The method of claim 1, wherein each of $R^{1a}$ and $R^{1b}$ is alkynyl.

11. The method of claim 1, wherein each of $R^{1a}$ and $R^{1b}$ is Ph.

12. The method of claim 1, wherein the compound is according to formula VIIIa, VIIIb, IXa, IXb, IXc, IXd, Xa, Xb, XI, XIIIa, XIIIb, XIIIc, XIIId, XIVa, XIVb, XIVc, XIVd, XVa, XVb, XVc, XVd, XVI, or XVII:

-continued

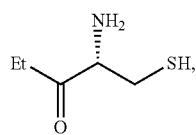
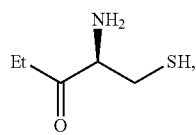
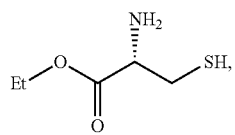
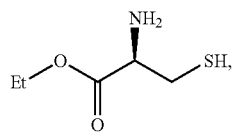
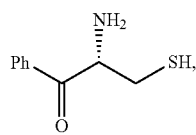
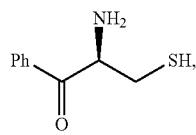
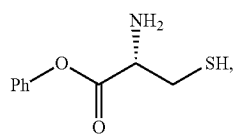
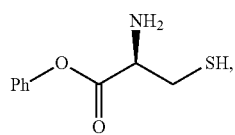

XIVa
XIVb
XIVc
XIVd
XVa
XVb
XVc
XVd

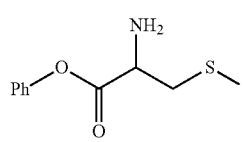 XVI or

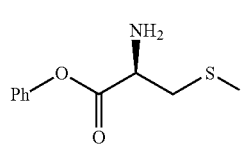 XVII;

or a pharmaceutically acceptable salt, solvate, cocrystal, or prodrug thereof, and stereoisomers, tautomers and isotopic variants thereof.

13. The method of claim 1, wherein the compound is one of the compounds listed in Table 1, wherein the compound # is 2, 9, 10, 12, or 14.

14. The method of claim 1, wherein the compound is according to formula IVa, IVb, IVc, IVd, IVe, Va, Vb, Vc, Vd, Ve, Vf, VIa, VIb, VIc, VId, VIIa, VIIb, VIIc, VIId, XIIa, or XIIb:

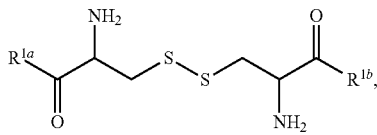 IVa

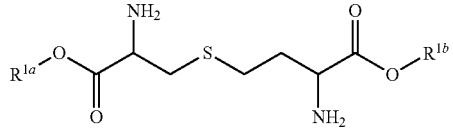 IVb

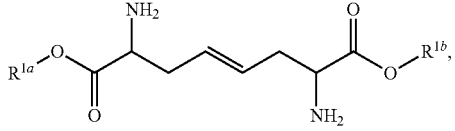 IVc

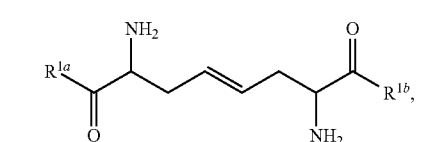 IVd

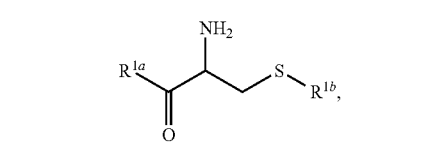 IVe

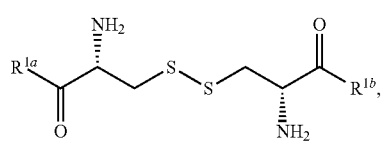 Va

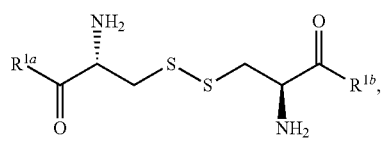 Vb

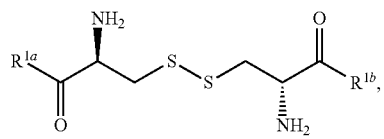 Vc

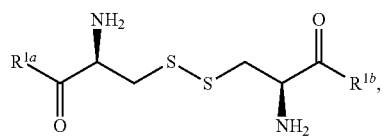 Vd

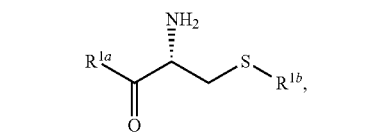 Ve

-continued
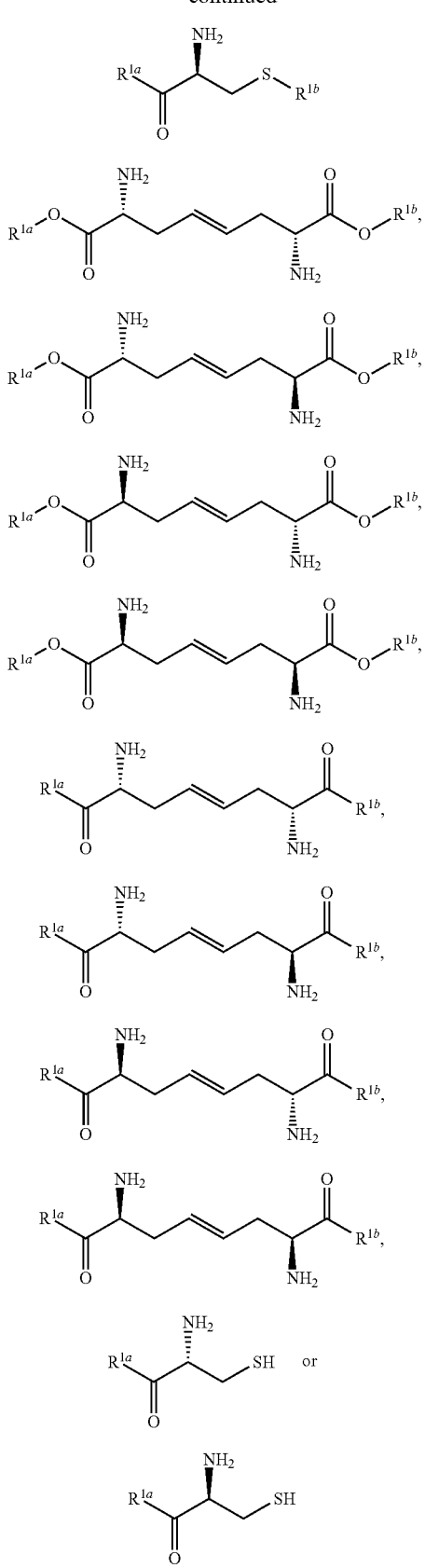
and wherein $R^{1a}$ and $R^{1b}$ are as in claim 1;
or a pharmaceutically acceptable salt, solvate, cocrystal, or prodrug thereof, and stereoisomers, tautomers and isotopic variants thereof.
15. The method of claim 1, wherein the compound is according to formula VIIIa, VIIIb, IXa, IXb, IXc, IXd, Xa, Xb, XI, XIIa, XIIb, XIIIa, XIIIb, XIVa, XIVb, XVa, XVb, XVI, or XVII:
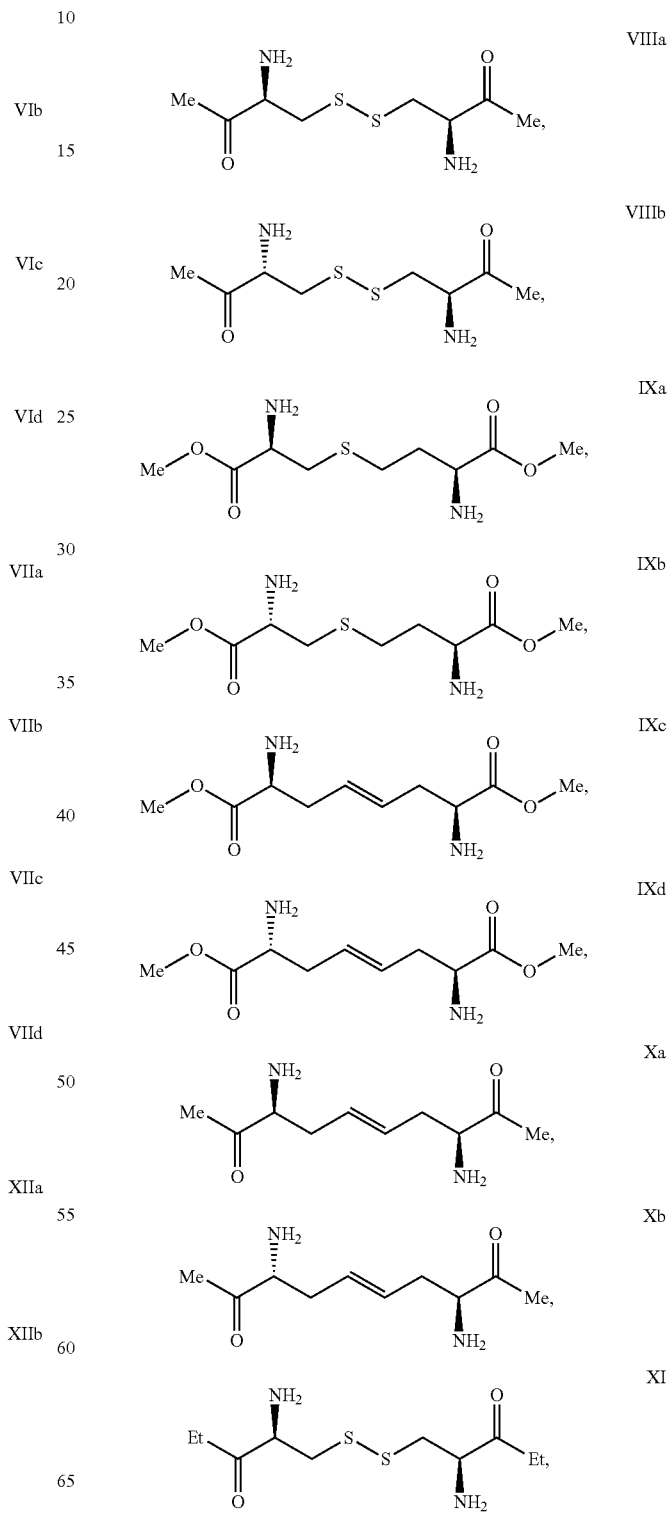

-continued

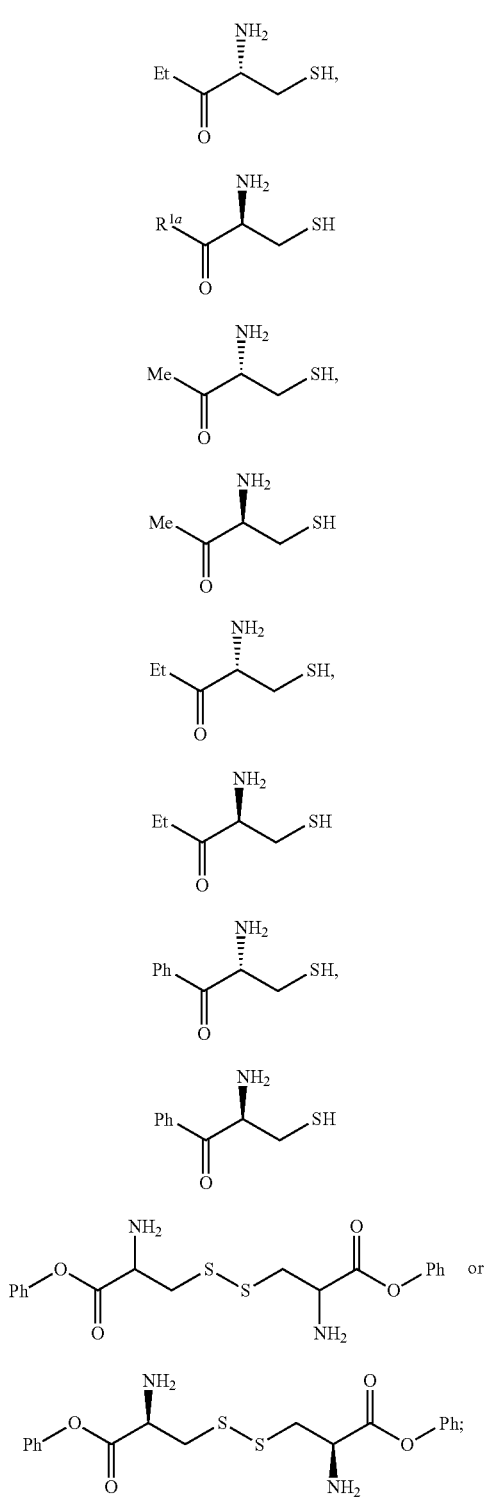

or a pharmaceutically acceptable salt, solvate, cocrystal, or prodrug thereof, and stereoisomers, tautomers and isotopic variants thereof.

16. A method for preventing, inhibiting or slowing the growth of L-cystine crystallization in a subject where such growth is present comprising administering to the subject an effective amount of a compound of formula IIIg:

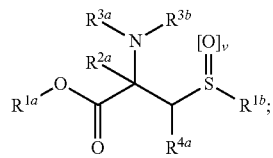

or a solvate, cocrystal, or prodrug thereof, and stereoisomers, tautomers and isotopic variants thereof; and wherein each $R^{1a}$ and $R^{1b}$ is independently selected from H, substituted or unsubstituted alkyl, substituted or unsubstituted alkenyl, substituted or unsubstituted alkynyl, substituted or unsubstituted aryl, substituted or unsubstituted aralkyl, and substituted or unsubstituted cycloalkyl;

each $R^{2a}$, $R^{3a}$, $R^{3b}$, and $R^{4a}$ is independently selected from H, substituted or unsubstituted alkyl, substituted or unsubstituted aryl, substituted or unsubstituted aralkyl, and substituted or unsubstituted cycloalkyl; and the subscript v is 0.

17. The method of claim 16, wherein the compound is according to formula Vg, Vh, XIIc, or XIId:

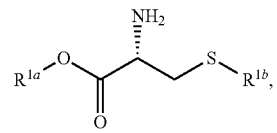

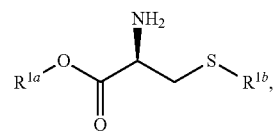

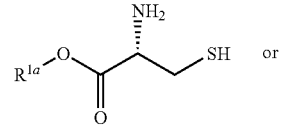

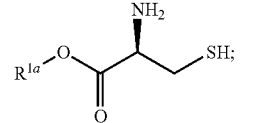

and wherein $R^{1a}$ is as in claim 16;

or a solvate, cocrystal, or prodrug thereof, and stereoisomers, tautomers and isotopic variants thereof.

18. The method of claim 16, wherein the compound is according to formula XIIIc, XIIId, XIVc, XIVd, XVc, or XVd:

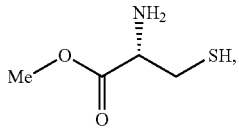

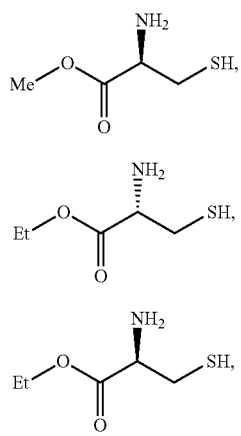
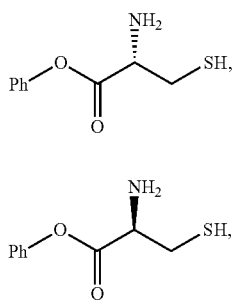
or a solvate, cocrystal, or prodrug thereof, and stereoisomers, tautomers and isotopic variants thereof.
\* \* \* \* \*